(12) United States Patent
Gonzalez et al.

(10) Patent No.: US 8,677,843 B2
(45) Date of Patent: Mar. 25, 2014

(54) SAMPLE ACQUISITION DEVICE

(75) Inventors: Bernard A. Gonzalez, St. Paul, MN (US); G. Marco Bommarito, Stillwater, MN (US); Paul J. Cobian, Woodbury, MN (US); Tera M. Nordby, Woodbury, MN (US); Tushar A. Kshirsagar, Woodbury, MN (US); Scott A. Burton, Woodbury, MN (US); Joseph J. Stoffel, Hastings, MN (US); Patrick A. Mach, Shorewood, MN (US); Gustavo H. Castro, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 510 days.

(21) Appl. No.: 12/867,146

(22) PCT Filed: Feb. 10, 2009

(86) PCT No.: PCT/US2009/033638
§ 371 (c)(1),
(2), (4) Date: Mar. 8, 2011

(87) PCT Pub. No.: WO2009/134509
PCT Pub. Date: Nov. 5, 2009

(65) Prior Publication Data
US 2011/0146419 A1 Jun. 23, 2011

Related U.S. Application Data

(60) Provisional application No. 61/029,063, filed on Feb. 15, 2008.

(51) Int. Cl.
*G01N 1/10* (2006.01)

(52) U.S. Cl.
USPC ...................................... 73/864.72

(58) Field of Classification Search
None
See application file for complete search history.

(56) References Cited

U.S. PATENT DOCUMENTS

| 2,490,168 A | 12/1949 | Strauss |
| 2,510,490 A | 6/1950 | Ager |

(Continued)

FOREIGN PATENT DOCUMENTS

| DE | 197 81 098 | 5/2005 |
| EP | 0 635 710 | 1/1995 |

(Continued)

OTHER PUBLICATIONS

Adamson, A.W.; Physical Chemistry of Surfaces; 4$^{th}$ Edition; 1982; pp. 12.

(Continued)

*Primary Examiner* — Robert R Raevis

(57) ABSTRACT

A sample acquisition device includes a capillary array configured to draw in a sample and retain the sample by capillary action. The capillary array may be coupled to an elongated member, such as a stem or a hollow tube, which defines a longitudinal axis extending in a first direction. In some embodiments, the capillary array defines a major sample acquisition surface that extends in a second direction different than the first direction. A ratio of the major sample acquisition surface area to maximum volume retained by the capillary array may be selected to minimize physical binding between the capillary array and sample. In some embodiments, the device may include a feedback mechanism to indicate the relative pressure applied to a sample source with the sample acquisition device. In addition, in some embodiments, the sample acquisition device may include a suction source to help draw the sample into the capillary array.

16 Claims, 24 Drawing Sheets

(56) References Cited

U.S. PATENT DOCUMENTS

| | | | |
|---|---|---|---|
| 3,004,681 | A | 10/1961 | Jinkens et al. |
| 3,163,160 | A | 12/1964 | Cohen |
| 3,252,331 | A | 5/1966 | Lancaster |
| 3,324,855 | A | 6/1967 | Heimlich |
| 3,450,129 | A | 6/1969 | Avery et al. |
| 3,495,917 | A | 2/1970 | Truhan |
| 3,640,268 | A | 2/1972 | Davis |
| 3,674,007 | A | 7/1972 | Freis |
| 3,773,035 | A | 11/1973 | Aronoff et al. |
| 3,776,220 | A | 12/1973 | Monaghan |
| 3,792,699 | A | 2/1974 | Tobin et al. |
| 3,890,204 | A | 6/1975 | Avery |
| 3,890,954 | A | 6/1975 | Greenspan |
| 3,915,806 | A | 10/1975 | Horlach |
| 3,918,435 | A | 11/1975 | Beall et al. |
| 3,923,604 | A | 12/1975 | Monaghan |
| 3,954,563 | A | 5/1976 | Mennen |
| 3,958,571 | A | 5/1976 | Bennington |
| 4,014,746 | A | 3/1977 | Greenspan |
| 4,014,748 | A | 3/1977 | Spinner et al. |
| 4,059,404 | A | 11/1977 | Schuster et al. |
| 4,175,008 | A | 11/1979 | White |
| 4,184,483 | A | 1/1980 | Greenspan |
| 4,196,167 | A | 4/1980 | Olsen |
| 4,223,093 | A | 9/1980 | Newman et al. |
| 4,311,792 | A | 1/1982 | Avery |
| 4,312,950 | A | 1/1982 | Snyder et al. |
| 4,329,990 | A | 5/1982 | Sneider |
| 4,353,868 | A | 10/1982 | Joslin et al. |
| 4,387,725 | A | 6/1983 | Mull |
| 4,409,988 | A | 10/1983 | Greenspan |
| 4,562,043 | A | 12/1985 | Mennen et al. |
| 4,586,604 | A | 5/1986 | Alter |
| 4,604,360 | A | 8/1986 | Hounsell |
| 4,635,488 | A | 1/1987 | Kremer |
| 4,653,510 | A | 3/1987 | Koll |
| 4,707,450 | A | 11/1987 | Nason |
| 4,770,853 | A | 9/1988 | Bernstein |
| 4,813,432 | A | 3/1989 | Saint-Amand |
| 5,713,843 | A | 2/1998 | Vangsness |
| 6,241,689 | B1 | 6/2001 | Chard et al. |
| 6,387,068 | B1 | 5/2002 | Naughton |
| 6,423,536 | B1* | 7/2002 | Jovanovich et al. ....... 435/287.2 |
| 6,503,013 | B2 | 1/2003 | Strauss |
| 6,514,224 | B1 | 2/2003 | Anapliotis |
| 6,547,467 | B2 | 4/2003 | Quintero |
| 6,779,938 | B1 | 8/2004 | Tsaur |
| 6,780,160 | B2 | 8/2004 | Zhou et al. |
| 6,811,341 | B2 | 11/2004 | Crane |
| 6,926,678 | B2 | 8/2005 | Cesarczyk |
| 7,022,289 | B1 | 4/2006 | Schlein et al. |
| 7,201,880 | B1 | 4/2007 | Heimberg et al. |
| 7,473,232 | B2 | 1/2009 | Teague |
| 2003/0038040 | A1 | 2/2003 | Bertl et al. |
| 2003/0041882 | A1 | 3/2003 | Joslyn |
| 2003/0191376 | A1 | 10/2003 | Samuels et al. |
| 2004/0010132 | A1 | 1/2004 | Rosen et al. |
| 2005/0011789 | A1 | 1/2005 | Tsaur |
| 2005/0112776 | A1* | 5/2005 | Clark et al. .................. 436/180 |
| 2005/0131314 | A1 | 6/2005 | Hird et al. |
| 2005/0132822 | A1* | 6/2005 | Massaro .................... 73/863.32 |
| 2006/0142668 | A1 | 6/2006 | Triva |
| 2007/0213634 | A1 | 9/2007 | Teague |

FOREIGN PATENT DOCUMENTS

| | | |
|---|---|---|
| EP | 1 308 130 | 5/2003 |
| WO | WO 2007/016618 | 2/2007 |
| WO | WO 2007/106691 | 2/2007 |
| WO | WO 2009/102835 | 8/2009 |

OTHER PUBLICATIONS

Adamson, A.W.; Physical Chemistry of Surfaces; 4$^{th}$ Edition; 1982; pp. 17.

Levine, N.S. et al.; "The Quantitative Swab Culture and Smear: A Quick, Simple method for Determining the Number of Viable Aerobic Bacteria on Open Wounds"; The Journal of Trauma; Vo. 16, No. 2; 1976; pp. 89-94.

* cited by examiner

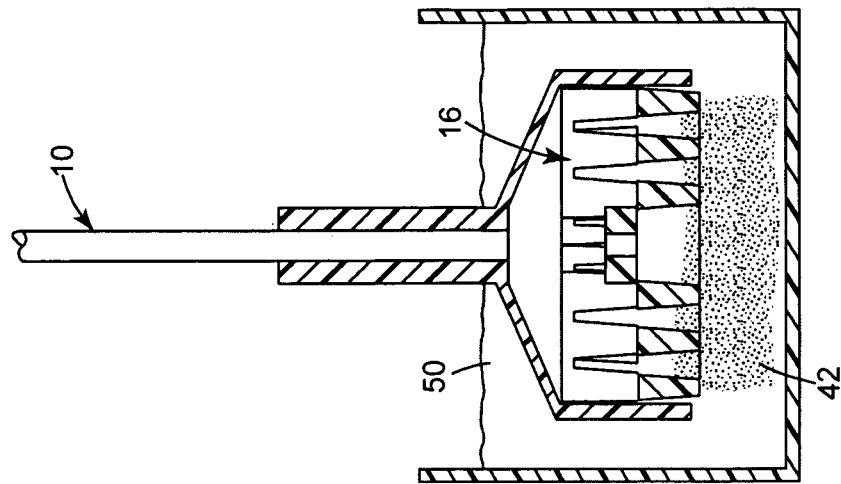
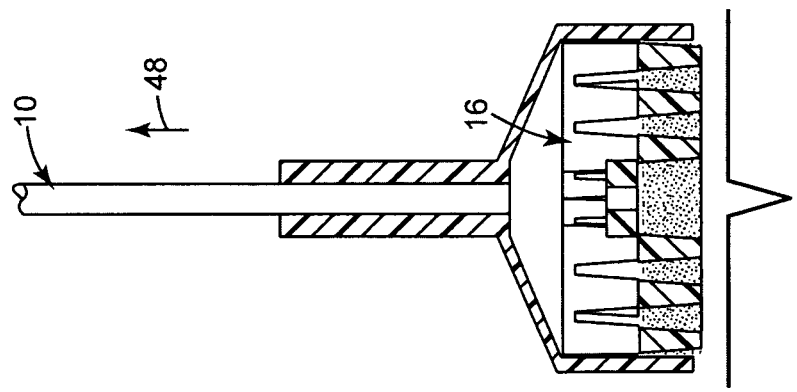
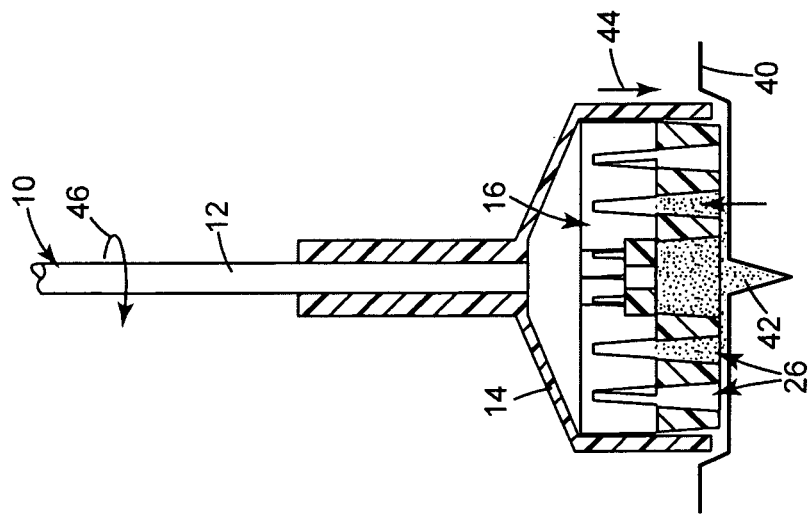

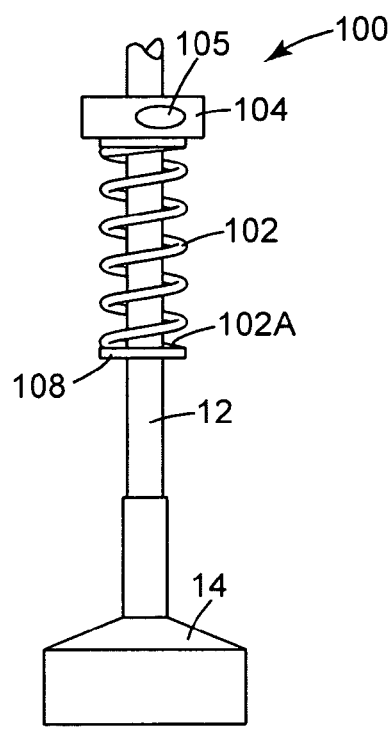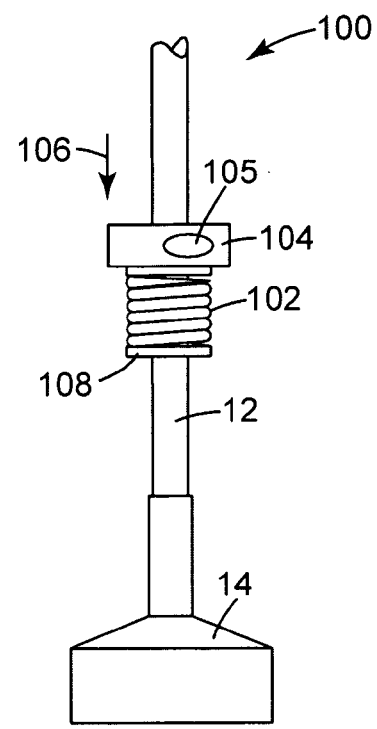
*Fig. 9A*  *Fig. 9B*
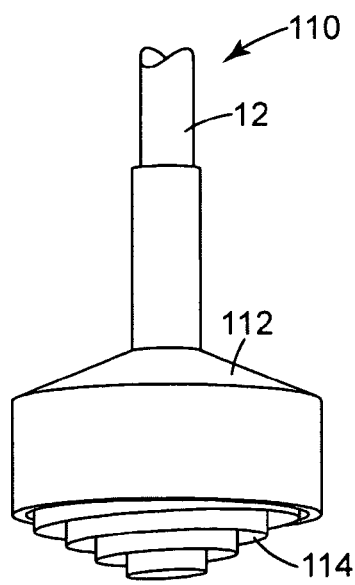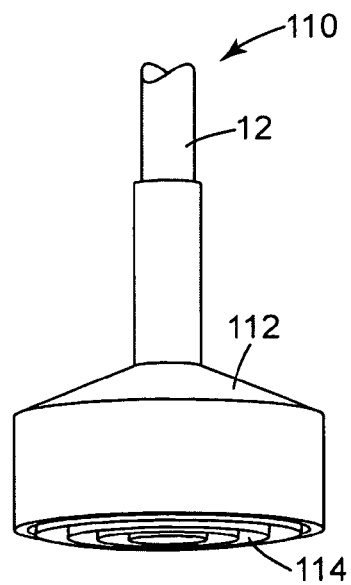
*Fig. 10A*  *Fig. 10B*

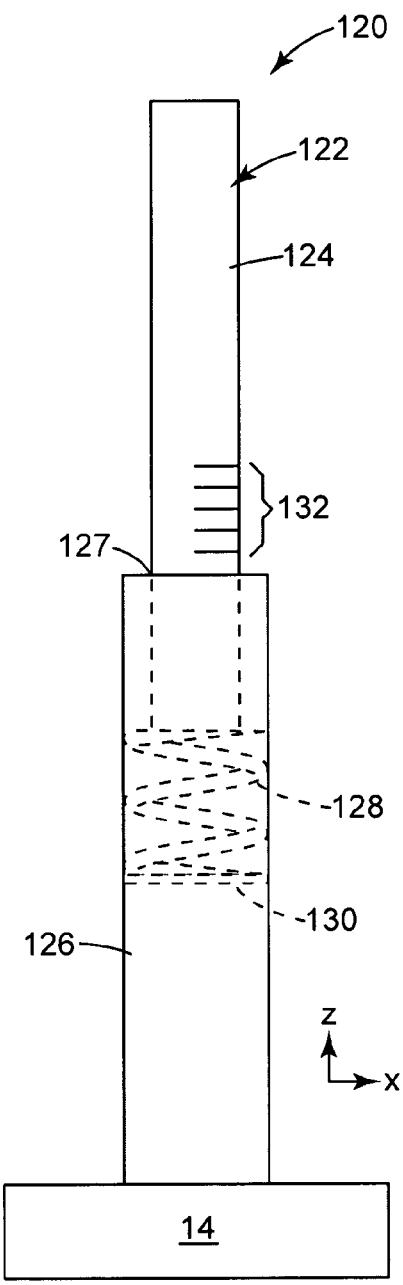
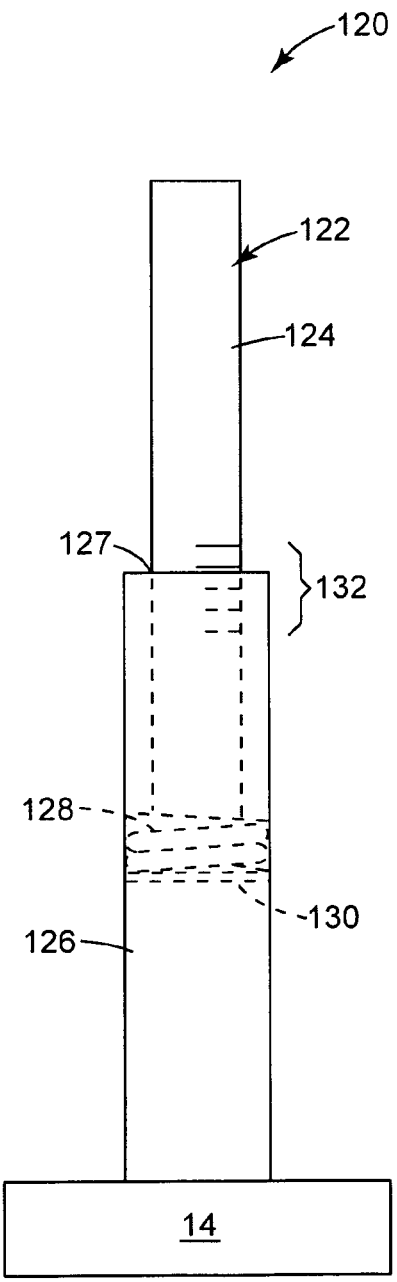
*Fig. 11A*  *Fig. 11B*

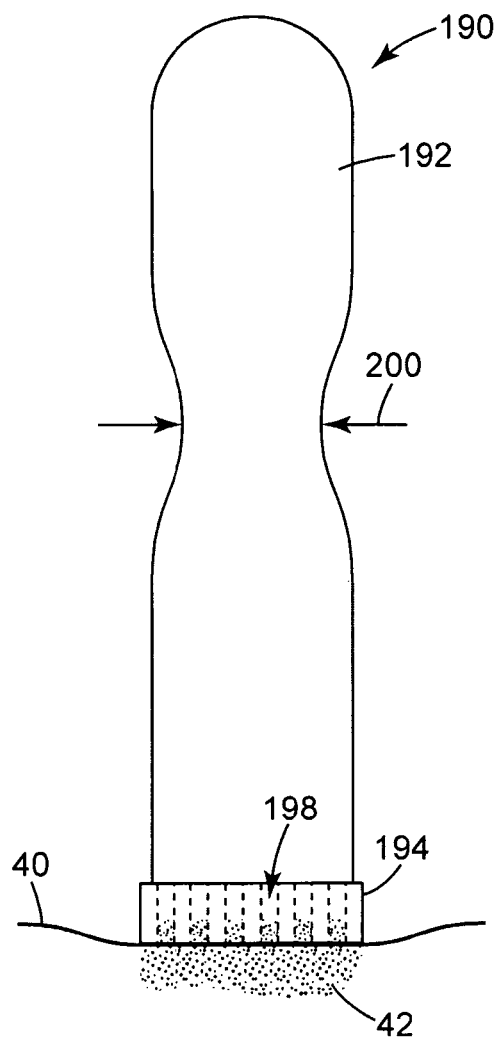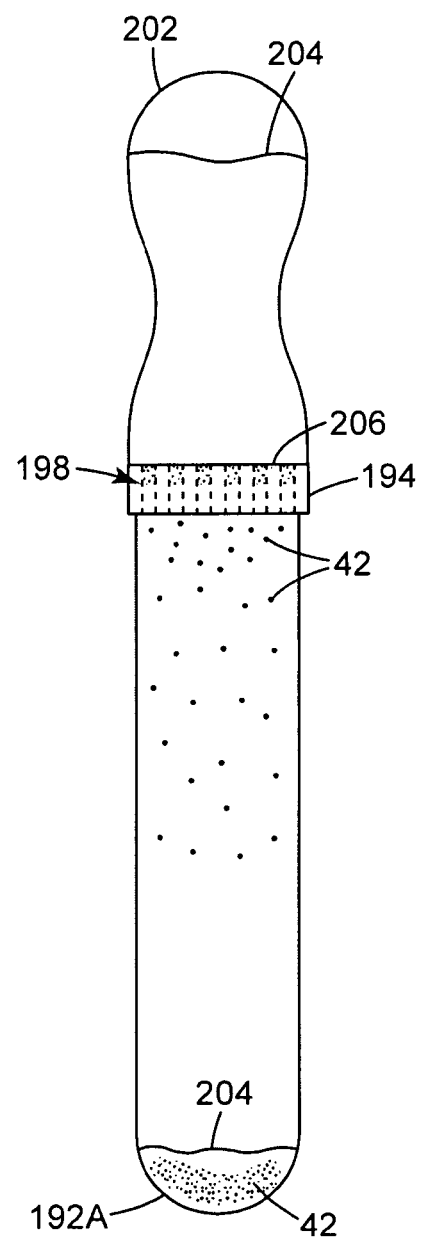
Fig. 20A
Fig. 20B

| Ex. | Device | Replicate | Aerobic Bacterial Count (CFUs/mL) | Average Aerobic Bacterial Count (CFUs/mL) |
|---|---|---|---|---|
| 1 | Rayon Swab | 1 | 170,000 | 250,000 |
| 2 | Rayon Swab | 2 | 270,000 | |
| 3 | Rayon Swab | 3 | 300,000 | |
| 4 | Capillary Array 250 (Fig. 17) | 1 | 100,000 | 200,000 |
| 5 | Capillary Array 250 (Fig. 17) | 2 | 280,000 | |
| 6 | Capillary Array 250 (Fig. 17) | 3 | 230,000 | |
| 7 | Capillary Array 194 (Fig. 18) | 1 | 300,000 | 230,000 |
| 8 | Capillary Array 194 (Fig. 18) | 2 | 150,000 | |
| 9 | Capillary Array 194 (Fig. 18) | 3 | 230,000 | |

*Fig. 21A*

| Ex. | Device | Aerobic Bacterial Count (CFUs/mL) |
|---|---|---|
| 10 | Rayon Swab | 350,000 |
| 11 | eSwab | 610,000 |
| 12 | Capillary Array 250 (Fig. 17) | 260,000 |
| 13 | Capillary Array 194 (Fig. 18) | 150,000 |

*Fig. 21B*

| Ex. | Device | Replicate | Aerobic Bacterial Count (CFUs/mL) | Average Aerobic Bacterial Count (CFUs/mL) |
|---|---|---|---|---|
| 14 | Rayon Swab | 1 | 380,000 | |
| 15 | Rayon Swab | 2 | 400,000 | 330,000 |
| 16 | Rayon Swab | 3 | 210,000 | |
| 17 | Capillary Array 250 (Fig. 17) | 1 | 1,300,000 | |
| 18 | Capillary Array 250 (Fig. 17) | 2 | 2,500,000 | 1,580,000 |
| 19 | Capillary Array 250 (Fig. 17) | 3 | 940,000 | |
| 20 | Capillary Array 194 (Fig. 18) | 1 | 4,000,000 | |
| 21 | Capillary Array 194 (Fig. 18) | 2 | 2,100,000 | 2,150,000 |
| 22 | Capillary Array 194 (Fig. 18) | 3 | 3,500,000 | |
| 23 | eSwab | 1 | 1,560,000 | 2,370,000 |
| 24 | eSwab | 2 | 3,180,000 | |

*Fig. 21C*

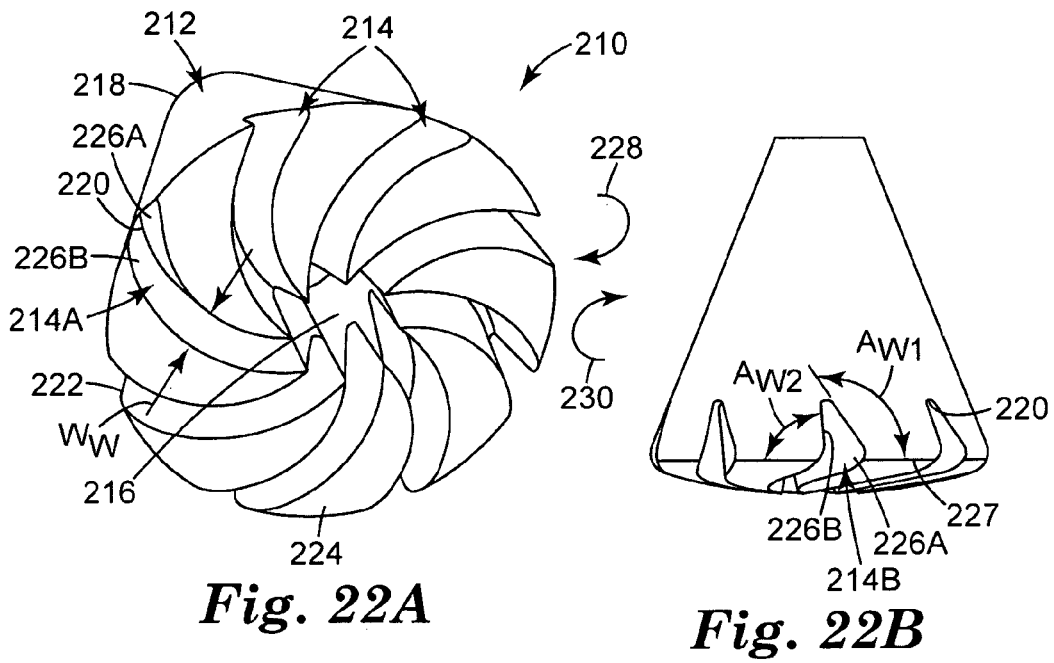
Fig. 22A  Fig. 22B
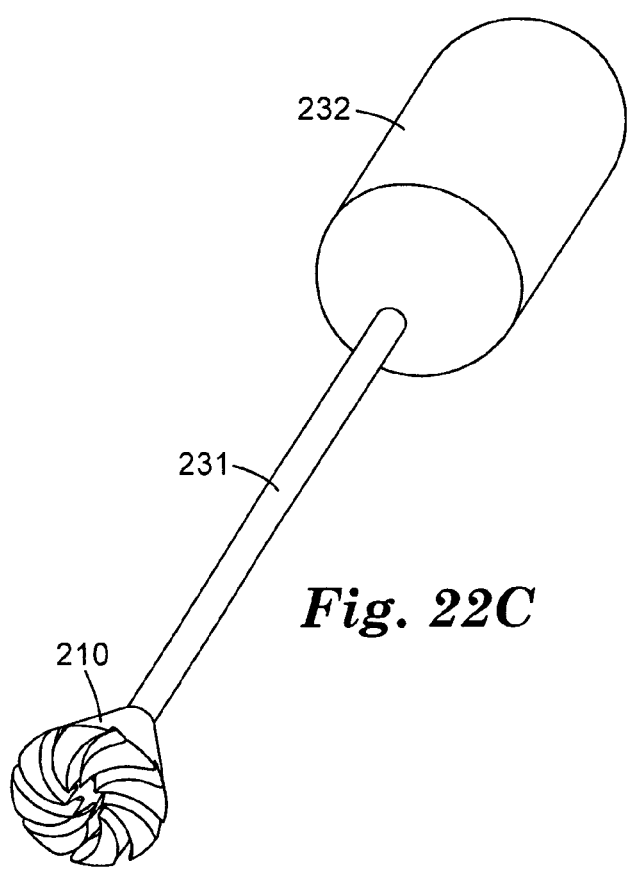
Fig. 22C

Fig. 25

| Sample Acquisition Device Type | Capillary Array Material | Elution Method | Weight (grams) | Eluted Bacterial Count(cfu/mL) | Normalized % Bacteria Released Compared to control |
|---|---|---|---|---|---|
| Capillary Array 250 (Fig. 17) | SLA Resin | Vortexing | 0.13 | 6520 | 105 |
| Capillary Array 250 (Fig. 17) | Polypropylene | Vortexing | 0.06 | 3080 | 101 |
| Capillary Array 250 (Fig. 17) | Polycarbonate | Vortexing | 0.13 | 3580 | 58 |
| Capillary Array 250 (Fig. 17 | Silicone Rubber | Vortexing | 0.04 | 1900 | 92 |
| Capillary Array 158 (Fig. 16B) | SLA Resin | Vortexing | 0.05 | 2520 | 100 |
| Capillary Array 150 (Fig. 16A) | SLA Resin | Vortexing | 0.12 | 6580 | 118 |
| Capillary Array 168 (Fig. 16C) | SLA Resin | Vortexing | 0.07 | 2980 | 94 |
| Capillary Array 178 (Fig. 16D) | SLA Resin | Vortexing | 0.01 | 1170 | 208 |
| Capillary Array 250 (Fig. 17) | SLA Resin | Lumen Flush | 0.13 | 8080 | 132 |
| Capillary Array 250 (Fig. 17) | Polypropylene | Lumen Flush | 0.06 | 3720 | 124 |
| Capillary Array 250 (Fig. 17) | Polycarbonate | Lumen Flush | 0.13 | 7300 | 122 |
| Capillary Array 250 (Fig. 17) | Silicone Rubber | Lumen Flush | 0.05 | 1300 | 53 |
| Capillary Array 158 (Fig. 16B) | SLA Resin | Lumen Flush | 0.05 | 3300 | 148 |
| Capillary Array 150 (Fig. 16A) | SLA Resin | Lumen Flush | 0.11 | 4350 | 80 |
| Capillary Array 168 (Fig. 16C) | SLA Resin | Lumen Flush | 0.05 | 2470 | 106 |
| Capillary Array 178 (Fig. 16D) | SLA Resin | Lumen Flush | 0.02 | 1470 | 141 |
| Capillary Array 250 (Fig. 17) | SLA Resin | Hand Twirling | 0.11 | 6400 | 118 |
| Capillary Array 250 (Fig. 17) | Polypropylene | Hand Twirling | 0.06 | 5480 | 200 |
| Capillary Array 250 (Fig. 17) | Polycarbonate | Hand Twirling | 0.14 | 9200 | 137 |
| Capillary Array 250 (Fig. 17) | Silicone Rubber | Hand Twirling | 0.04 | 1550 | 89 |
| Capillary Array 158 (Fig. 16B) | SLA Resin | Hand Twirling | 0.07 | 6300 | 1.81 |
| Capillary Array 150 (Fig. 16A) | SLA Resin | Hand Twirling | 0.05 | 2920 | 119 |
| Capillary Array 168 (Fig. 16C) | SLA Resin | Hand Twirling | 0.05 | 3180 | 125 |
| Capillary Array 178 (Fig. 16D) | SLA Resin | Hand Twirling | 0.02 | 1520 | 193 |
| Control | NA | NA | 0.10 | 4800 | 100 |

| Parameter Type | Parameter Value | Average of Normalized % Bacteria Released Compared To Control | Standard Deviation | Average of Weight (grams) | Standard Deviation |
|---|---|---|---|---|---|
| Elution method | Vortexing | 110 | 43 | NA | NA |
| Elution method | Lumen Flush | 113 | 32 | NA | NA |
| Elution method | Hand Twirling | 145 | 41 | NA | NA |
| Design | Capillary Array 250 (Fig. 17) | 118 | 13 | 0.12 | 0.01 |
| Design | Capillary Array 158 (Fig. 16B) | 143 | 41 | 0.06 | 0.01 |
| Design | Capillary Array 150 (Fig. 16A) | 106 | 22 | 0.09 | 0.04 |
| Design | Capillary Array 168 (Fig. 16C) | 108 | 16 | 0.06 | 0.01 |
| Design | Capillary Array 178 (Fig. 16D) | 181 | 35 | 0.02 | 0.01 |
| Material (Capillary Array 250 (Fig. 17)) | SLA Resin (surface energy ~50 dynes/cm) | 118 | 13 | 0.12 | 0.01 |
| Material (Capillary Array 250 (Fig. 17)) | Polypropylene (surface energy ~30 dynes/cm) | 142 | 52 | 0.06 | 0.00 |
| Material (Capillary Array 250 (Fig. 17)) | Polycarbonate (surface energy ~45 dynes/cm) | 106 | 42 | 0.13 | 0.01 |
| Material (Capillary Array 250 (Fig. 17)) | Silicone rubber (surface energy ~20 dynes/cm) | 78 | 22 | 0.04 | 0.01 |

Fig. 26

SAMPLE ACQUISITION DEVICE

CROSS REFERENCE TO RELATED APPLICATIONS

This application claims the benefit to U.S. Provisional Application Ser. No. 61/029,063, filed Feb. 15, 2008, which is incorporated herein by reference.

This invention was made with United States government support awarded by the following agency under Contract No. W81XWH-07-01-0354. The United States government has certain rights in this invention.

TECHNICAL FIELD

The invention relates to sample analysis, and, more particularly, a sample acquisition device.

BACKGROUND

A biological specimen from a living (e.g., a human patient) or nonliving source (e.g., a food preparation surface) may be obtained via a sample acquisition device for bioburden testing. Bioburden testing may include, for example, the determination of the number of organisms with which the specimen is contaminated. For example, a sample from a patient's open wound may be acquired in order to determine whether the wound is contaminated with potentially hazardous microorganisms.

One type of conventional sample acquisition device is a medical swab with a fibrous nonwoven (e.g., rayon) tip at one end of a stem. A user may manually handle the swab by grasping the stem and placing the swab tip in contact with selected tissue cells or other biological specimens, e.g., from within the ear, nose, throat or open wound of a patient. Some of targeted tissue cells or biological specimens adhere to the swab tip, thereby defining a biological sample for analysis. Tests that may be performed with the acquired sample include, for example, fluorescent tests, enzymatic tests, monoclonal based tests, agglutination tests, and the like.

SUMMARY

In general, the invention is directed to a sample acquisition device including a capillary array configured to draw in a sample and retain the sample by capillary pressure. The capillary array defines one or more capillaries that define a maximum sample volume. A capillary may be, for example, a sample acquisition region that obtains and retains a sample by capillary pressure. In some embodiments, the capillary array may include a plurality of interconnected structures that defines a common capillary. In other embodiments, the capillary array comprises a plurality of separate sample acquisition regions that are not in fluidic communication with each other.

The capillary array may be coupled to an elongated member, such as a stem or a hollow tube, which defines a longitudinal axis extending in a first direction. In some embodiments, the capillary array defines a major sample acquisition surface that extends in a second direction different than the first direction. A ratio of the total sample contact regions of the capillary array and the maximum sample volume retained by the capillary array may be selected to minimize physical binding between the capillary array and sample.

In some embodiments, the elongated member may be fluidically coupled to the capillary array. A fluid may be introduced into elongated member to elute the sample from the capillary array. For example, in some embodiments, a bulb storing a rinse fluid may be coupled to a first end of the elongated member and the capillary array may be coupled to an opposite end. In other embodiments, a bulb storing a rinse fluid may be coupled to the same end of the elongated member as capillary array.

In some embodiments, the device may include a feedback mechanism to indicate the relative pressure applied to a sample source with the sample acquisition device. In addition, in some embodiments, the sample acquisition device may include a suction source to help draw the sample into the capillary array. For example, in one embodiment, a hollow tube in fluidic communication with the capillary array may help aspirate a sample into the capillary array.

In one aspect, the invention is directed to a sample acquisition device comprising a stem defining a longitudinal axis extending in a first direction, and a capillary array coupled to the stem, wherein the capillary array comprises a major sample acquisition surface extending along a second direction different than the first direction.

In another aspect, the invention is directed to a sample acquisition device comprising an elongated member defining an inner lumen, and a capillary array in fluidic communication with the inner lumen. The capillary array defines at least one capillary that receives a sample from a sample source. The sample acquisition device further comprises a fluid distribution member disposed between the inner lumen of the elongated member and the capillary array. The inner lumen may comprise one lumen or a plurality of lumens.

In another aspect, the invention is directed to a sample acquisition device comprising a stem, and a capillary array coupled to the stem and comprising a plurality of grooves. At least one of the grooves comprises a first wall and a second wall oriented substantially nonparallel to the first wall.

In another aspect, the invention is directed to a sample acquisition device comprising a stem, a capillary array coupled to the stem, and a tactile feedback mechanism that indicates a relative amount of pressure applied by a user when engaging the capillary array with a sample source.

In another aspect, the invention is directed to a method comprising holding a stem of a sample acquisition device, the sample acquisition device further comprising a capillary array coupled to the stem, wherein the capillary array comprises a major sample acquisition surface extending along a second direction different than the first direction, and placing the capillary array in contact with a sample source to acquire a sample.

In another aspect, the invention is directed to a method comprising placing a capillary array of a sample acquisition device in contact with a sample source and rotating the capillary array in a first direction to acquire a sample. The method may further comprise withdrawing the sample acquisition device from the sample source and rotating the capillary array in a second direction to release the sample from the sample acquisition device, wherein the second direction is substantially opposite the first direction.

In another aspect, the invention is directed to a sample acquisition device comprising a suction source or a pressure source to absorb or expel either the acquired sample or the stored sample, and a capillary array in fluidic communication with the suction source, wherein the capillary array comprises a plurality of sample acquisition regions, wherein the capillary array is configured to hold a sample volume of about 0.025 milliliters (mL) to about 0.500 mL.

In another aspect, the invention is directed to a method comprising placing a capillary array of a sample acquisition device in contact with a sample source to acquire a sample, wherein the capillary array is configured to hold a sample volume of about 0.025 milliliters to about 0.500 milliliters and comprises a plurality of sample acquisition regions, the sample acquisition device further comprising a suction source in fluidic communication with each of the sample acquisition regions. The method further comprises applying suction to the sample source with the suction source to draw sample into the capillary array.

Exemplary Embodiments

The following lists exemplary embodiments of the present invention:

1. A sample acquisition device comprising a stem defining a longitudinal axis extending in a first direction; and a capillary array coupled to the stem, wherein the capillary array comprises a major sample acquisition surface extending along a second direction different than the first direction.

2. The sample acquisition device of embodiment 1, wherein the second direction is substantially perpendicular to the first direction.

3. The sample acquisition device of embodiment 1, wherein at least a portion of the major sample acquisition surface is curvilinear.

4. The sample acquisition device of embodiment 1, wherein the capillary array comprises a plurality of structures defining a common sample acquisition region.

5. The sample acquisition device of embodiment 1, wherein the capillary array defines a plurality of sample acquisition regions.

6. The sample acquisition device of embodiment 1, wherein the capillary array defines a plurality of concentric capillary channels.

7. The sample acquisition device of embodiment 1, wherein the capillary array defines a sample acquisition channel, and a width of the sample acquisition channel along the sample acquisition surface is about 0.25 millimeters to about 1.5 millimeters.

8. The sample acquisition device of embodiment 1, wherein the capillary array defines a sample acquisition channel, and a greatest height of the sample acquisition channel measured along the first direction is about 0.1 millimeters to about 15 millimeters.

9. The sample acquisition device of embodiment 1, wherein the sample acquisition surface has an area of about 0.1 square centimeters ($cm^2$) to about 1.5 $cm^2$.

10. The sample acquisition device of embodiment 1, wherein a ratio of the greatest dimension of the sample acquisition surface to a greatest dimension of the capillary array along the first direction is about 3:1 to about 100:1.

11. The sample acquisition device of embodiment 1, wherein the capillary array is configured to retain a maximum sample volume of about 0.025 milliliters to about 0.500 milliliters.

12. The sample acquisition device of embodiment 1, wherein the capillary array is configured to retain a maximum sample volume, wherein a ratio of an area of the sample acquisition surface to the maximum sample volume is about 0.2 square centimeters per milliliter ($cm^2/mL$) to about 60 $cm^2/mL$.

13. The sample acquisition device of embodiment 1, wherein the capillary array is formed of a material comprising at least one of polysulfone, polycarbonate, polytetrafluoroethylene, polyvinylidene difluoride or nylon.

14. The sample acquisition device of embodiment 1, wherein the capillary array comprises a molded structure.

15. The sample acquisition device of embodiment 1, wherein the capillary array comprises a material comprising a surface energy of at least 20 dynes/centimeter.

16. The sample acquisition device of embodiment 15, wherein the surface energy is less than or equal to about 82 dynes/centimeter.

17. The sample acquisition device of embodiment 1, wherein the stem is in fluidic communication with the capillary array.

18. The sample acquisition device of embodiment 1, further comprising a fluid chamber in fluidic communication with the capillary array.

19. The sample acquisition device of embodiment 1, further comprising a tip coupled to the capillary array, wherein the tip defines a rounded sample acquisition surface.

20. The sample acquisition device of embodiment 1, further comprising a tip coupled to the capillary array, wherein the tip comprises a flexible portion that extends away from the sample acquisition surface.

21. The sample acquisition device of embodiment 1, further comprising a tactile feedback mechanism that indicates a relative amount of pressure applied by a user when engaging the capillary array with a sample source.

22. The sample acquisition device of embodiment 1, wherein the capillary array comprises a reagent.

23. The sample acquisition device of embodiment 1, further comprising a suction source in fluidic communication with the capillary array.

24. The sample acquisition device of embodiment 1, wherein the common member defines a plurality of grooves, wherein at least one of the grooves comprises a wall oriented at a nonorthogonal angle relative to the major sample acquisition surface.

25. The sample acquisition device of embodiment 24, wherein the wall comprises a first wall and the at least one of the grooves comprises a second wall, the first and second walls converging at an apex.

26. The sample acquisition device of embodiment 24, wherein the wall comprises a first wall and the at least one of the grooves at comprises a second wall oriented substantially nonparallel to the first wall.

27. The sample acquisition device of embodiment 24, wherein each groove of the plurality of grooves is curvilinear along the sample acquisition surface, and the plurality of grooves curve in substantially the same direction.

28. A sample acquisition device comprising an elongated member defining an inner lumen; a capillary array in fluidic communication with the inner lumen, wherein the capillary array defines at least one capillary that receives a sample from a sample source; and a fluid distribution member disposed between the inner lumen of the elongated member and the capillary array.

29. A sample acquisition device comprising a stem; and a capillary array coupled to the stem and comprising a plurality of grooves, wherein at least one of the grooves comprises a first wall and a second wall oriented substantially nonparallel to the first wall.

30. The sample acquisition device of embodiment 29, wherein the first and second walls converge at an apex.

31. The sample acquisition device of embodiment 30, wherein the apex comprises a round surface.

32. The sample acquisition device of embodiment 29, wherein each groove of the plurality of grooves is curvilinear along a sample acquisition surface of the capillary array and the plurality of grooves curve in substantially the same direction.

33. The sample acquisition device of embodiment 32, wherein the plurality of grooves comprises a substantially similar radius of curvature.

34. The sample acquisition device of embodiment 29, wherein the plurality of grooves radiate outward from a common center portion of the capillary array.

35. The sample acquisition device of embodiment 29, wherein the plurality of grooves are in fluidic communication with each other.

36. The sample acquisition device of embodiment 29, wherein the first wall is oriented at an angle of about 20° to about 160° relative to the second wall.

37. The sample acquisition device of embodiment 36 wherein the first wall is oriented at an angle of about 45° to about 135° relative to the second wall.

38. The sample acquisition device of embodiment 29, wherein the second wall defines an inclined surface into a respective one of the sample acquisition regions when the body is rotated in a first direction relative to a sample acquisition surface.

39. A sample acquisition device comprising a stem; a capillary array coupled to the stem; and a tactile feedback mechanism that indicates a relative amount of pressure applied by a user when engaging the capillary array with a sample source.

40. The sample acquisition device of embodiment 39, wherein the tactile feedback mechanism comprises a spring that compresses as the user engages the capillary array with the sample source.

41. The sample acquisition device of embodiment 40, wherein the stem comprises a first portion and a second portion movable relative to the first portion, wherein the spring is disposed between the first and second portions of the stem.

42. The sample acquisition device of embodiment 41, wherein at least one of the first or second portions comprising a visible marker to indicate relative movement between the first and second portions of the stem.

43. The sample acquisition device of embodiment 39, wherein capillary array is deformable, and the tactile feedback comprises the deformable capillary array.

44. A method comprising holding a stem of a sample acquisition device, the sample acquisition device further comprising a capillary array coupled to the stem, wherein the capillary array comprises a major sample acquisition surface extending along a second direction different than the first direction; and placing the capillary array in contact with a sample source to acquire a sample.

45. The method of embodiment 44, wherein the capillary array is in fluidic communication with the stem, the method further comprising introducing a fluid into the stem to elute the sample from the capillary array.

46. The method of embodiment 45, wherein introducing the fluid into the stem comprises releasing the fluid from a bulb that is coupled to the stem.

47. A method comprising placing a capillary array of a sample acquisition device in contact with a sample source; rotating the capillary array in a first direction to acquire a sample; withdrawing the sample acquisition device from the sample source; and rotating the capillary array in a second direction to release the sample from the sample acquisition device, wherein the second direction is substantially opposite the first direction.

48. The method of embodiment 47, further comprising at least partially submerging the capillary array in a rinse fluid prior to rotating the capillary array in the second direction.

49. A sample acquisition device comprising a suction source; and a capillary array in fluidic communication with the suction source, wherein the capillary array comprises a plurality of sample acquisition regions, wherein the capillary array is configured to hold a sample volume of about 0.025 milliliters to about 0.500 milliliters.

50. The sample acquisition device of embodiment 49, wherein the suction source comprises a compressible tube, wherein the capillary array is disposed at an end of the compressible tube.

51. The sample acquisition device of embodiment 49, wherein the suction source comprises a syringe.

52. The sample acquisition device of embodiment 49, further comprising a fluid chamber configured to couple to the capillary array.

53. The sample acquisition device of embodiment 49, wherein the capillary array comprises a plurality of apertures.

54. The sample acquisition device of embodiment 49, wherein the capillary array defines a curvilinear major sample acquisition surface.

55. The sample acquisition device of embodiment 49, wherein the suction source comprises a longitudinal axis extending in a first direction and the capillary array defines a major sample acquisition surface extending in a second direction different than the first direction.

56. The sample acquisition device of embodiment 55, wherein the sample acquisition surface has an area of about 0.1 square centimeters ($cm^2$) to about 1.5 $cm^2$.

57. The sample acquisition device of embodiment 49, wherein a ratio of an area of the sample acquisition surface to the maximum sample volume is about 0.2 square centimeters per milliliter ($cm^2/mL$) to about 60 $cm^2/mL$.

58. The sample acquisition device of embodiment 49, wherein the capillary array is formed of a material comprising at least one of polysulfone, polycarbonate, polytetrafluoroethylene, polyvinylidene difluoride or nylon 59. The sample acquisition device of embodiment 49, wherein the capillary array comprises a molded structure.

60. The sample acquisition device of embodiment 49, wherein the capillary array comprises a material comprising a surface energy of at least 20 dynes/centimeter.

61. The sample acquisition device of embodiment 60, wherein the surface energy is less than or equal to about 82 dynes/centimeter.

62. The sample acquisition device of embodiment 49, further comprising a reagent disposed on the capillary array.

63. A method comprising placing a capillary array of a sample acquisition device in contact with a sample source to acquire a sample, wherein the capillary array is configured to hold a sample volume of about 0.025 milliliters to about 0.500 milliliters and comprises a plurality of sample acquisition regions, the sample acquisition device further comprising a suction source in fluidic communication with each of the sample acquisition regions; and applying suction to the sample source with the suction source to draw the sample into at least some of the sample acquisition regions.

64. The method of embodiment 63, wherein the sample acquisition device further comprises a tube defining an inner lumen in fluidic communication with the capillary array, the method further comprising introducing a fluid into the inner lumen to elute the sample from the capillary array.

65. The method of embodiment 64, wherein applying suction to the sample source comprises compressing the tube.

66. The method of embodiment 64, further comprising coupling a fluid source to the capillary array.

67. The method of embodiment 64, wherein at least two of the plurality of sample acquisition regions are not in fluidic communication with each other.

68. A sample acquisition device comprising a stem defining a longitudinal axis extending in a first direction; and a capillary array coupled to the stem, wherein the capillary array defines a plurality of capillary channels in fluidic communication with each other.

69. The sample acquisition device of embodiment 68, wherein the capillary channels are defined by walls extending substantially along the first direction.

70. The sample acquisition device of embodiment 68, wherein the walls define substantially concentric circles along a sample acquisition surface of the capillary array.

The details of one or more embodiments of the invention, including but not limited to the exemplary embodiments listed above, are set forth in the accompanying drawings and the description below. Other features, objects, and advantages of the invention will be apparent from the description and drawings, and from the claims.

BRIEF DESCRIPTION OF DRAWINGS

FIGS. 5A-5C illustrate a technique for acquiring a sample with the sample acquisition device of FIG. 1.

FIGS. 9A-10B are perspective views of embodiments of sample acquisition devices, which each include a tactile feedback to indicate relative pressure applied to a sample source.

FIGS. 11A-11B illustrate another embodiment of a sample acquisition device, which includes markers for indicating the relative pressure applied to a sample source with the device.

FIGS. 20A-20B illustrate a technique for acquiring a sample with the sample acquisition device of FIG. 18.

FIGS. 21A-21C illustrate the results of an experiment in which three different sample acquisition devices were swabbed at different points on a cheek of a human subject using the Levine technique.

FIGS. 22A and 22B are schematic illustrations of a capillary array that includes a body defining a plurality of interconnected grooves.

FIG. 22C is a schematic perspective view of the capillary array of FIG. 22A coupled to a stem and suction source.

FIGS. 25 and 26 are tables illustrating the results of an experiment in which sample acquisition devices including different types of capillary arrays, some of which were formed of different materials, were evaluated for acquisition and release characteristics.

DETAILED DESCRIPTION

Figure 1:
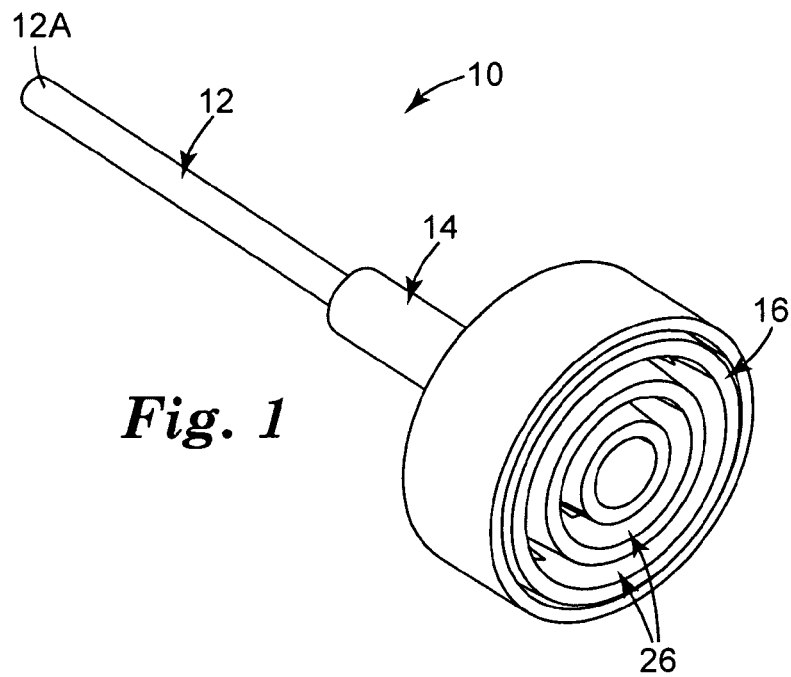
FIG. 1 is a perspective view of an embodiment of a sample acquisition device.
Figure 2:
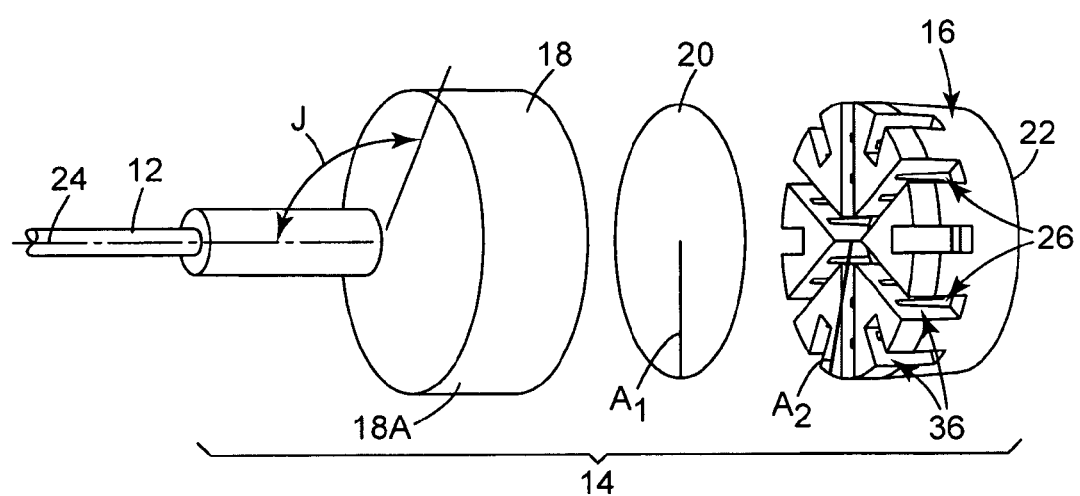
FIG. 2 is a schematic exploded view of the sample acquisition device of FIG. 1.

FIG. 1 is a perspective view of sample acquisition device 10, which includes stem 12, head 14, and capillary array 16, which may be directly or indirectly coupled to head 14. FIG. 2 is an exploded perspective view of sample acquisition device 10. As shown in FIG. 2, head 14 includes holding member 18 configured to hold flow distributor 20 and capillary array 16 in a generally fixed position relative to each other, as well as to mechanically couple head 14 to stem 12. In the embodiment of sample acquisition device 10 shown in FIGS. 1 and 2, holding member 18 is attached to stem 12 via an interference fit. In other embodiments, holding member 18 may be mechanically coupled to stem 12 via other suitable methods, such as via adhesive, interlocking parts (e.g., stem 12 may include a notch that fits within a groove defined by holding member 18), welding (e.g., ultrasonic welding) or combinations thereof.

Sample acquisition device 10 is useful for acquiring a quantity of a sample from a sample source. As described in further detail below, a user may place capillary array 16 in contact with a sample source in order to obtain a sample, such as a liquid, solid or partially liquid and solid sample, from the sample source. The sample source may be from a living or nonliving patient. Examples of living sources include, but are not limited to, a human patient's wound, ear, nose, throat, and the like. Examples of nonliving sources include, but are not limited to, a food preparation surface or utensil.

The sample acquired via sample acquisition device 10 may be used for any suitable purpose. In some embodiments, the sample may be analyzed. For example, in one embodiment, the sample may be tested for bioburden, e.g., the number of microorganisms present in the sample, or for the presence of target microorganisms (e.g., *Staphylococcus aureus*). Other example procedures that may be conducted with the sample acquired via sample acquisition device 10 includes preparation of a biological sample for, for example, DNA sequencing, and/or detection, diagnostic or analytical procedures, chemical, biological or biochemical reactions, and the like. Examples of such reactions include detection via thermal processing techniques, such as, but not limited to, enzyme kinetic studies, homogeneous ligand binding assays, and more complex biochemical or other processes that require precise thermal control and/or rapid thermal variations. Other examples of tests performed with an acquired sample include fluorescent tests, enzymatic tests, monoclonal based tests, agglutination tests, and the like.

Stem 12 may be any elongated member defining a structure that a user may manually grasp in order to place capillary array 16 in contact with a sample source. Stem 12 may be formed of any suitable material that exhibits sufficient rigidity to enable the user to control the position of capillary array 16 relative to a sample source, as well as hold capillary array 16 adjacent to the sample source with some pressure. For example, stem 12 may be formed of paper (e.g., cardboard), a polymer, steel (e.g., stainless steel), a metal alloy, and the like.

Head 14 comprises capillary array 16, which is coupled to stem 12 by holding member 18, and flow distributor 20, which is disposed within head 14. Holding member 18 defines an opening configured to receive capillary array 16, and helps capillary array 16 retain a sample by defining an enclosure that substantially surrounds portions of capillary array 16. In the embodiment shown in FIGS. 1 and 2, holding member 18 substantially surrounds portions of capillary array 16 such that sample acquisition surface 22 is exposed. In other embodiments, however, head 14 may not include holding member 18, and capillary array 16 may be directly attached to stem 12. Alternatively, stem 12 and holding member 18 may be substantially integral, i.e., formed from a single piece of material or formed to define a substantially uniform structure (e.g., by ultrasonic welding or another attachment means that substantially eliminates seams between head 18 and stem 12).

Capillary array 16 may be any suitable structure that defines at least one capillary structure that obtains and retains a sample from a sample source by capillary pressure. In one embodiment, capillary array 16 defines a single capillary, e.g., a plurality of structures that define a common sample acquisition region that acquires a sample via capillary action. In other embodiments, capillary array 16 includes a plurality of structures that define separate capillaries, i.e., separate sample acquisition regions that are not in fluidic communication, where the separate regions acquire a sample via capillary action. Regardless of whether capillary array 16 comprises one or more sample acquisition regions, the one or more sample acquisition regions of capillary array 16 are designed to retain a maximum sample volume. The maximum sample volume may be selected, for example, based on the sample analysis tests performed with the sample.

Capillary array 16 acquires sample particles from a sample source with the aid of capillary force, which may be a consequence of surface energy. The surface energy of the capillary array material may be selected based on the surface energy of the sample particles. It may be desirable to select a capillary array material that exhibits a surface energy that results in a sufficient attraction to the sample particles, regardless of the solid or liquid state of the sample, in order to draw the sample into capillary array 16 and hold the sample in sample acquisition device 10. In this way, capillary array acquires a sample and acts as a repository to hold the sample.

Capillary array 16 is designed (e.g., a size and material of capillary array 16 may be configured) to provide a suitable amount of capillary pressure when capillary array 16 is in contact with a sample that is less than the capillary pressure in capillary array 16. The term "capillary pressure" ($P_r$) may refer to the pressure drop $\Delta P$ needed to achieve a capillary rise of a sample into capillary array 16 and is given by:

$$\Delta P = P_C (2 * \gamma * \cos \theta * h)/a^2$$

Where $\gamma$ is the surface tension of the sample, $\theta$ is the contact angle the sample makes with, for example, sample acquisition surface 22 of capillary array 16, and "a" is the capillarity constant as defined by Adamson in Physical Chemistry of Surfaces (4$^{th}$ Ed., p. 12). The capillary pressure can be measured by using the Capillary Rise Method also described by Adamson in Physical Chemistry of Surfaces (4.sup.th Edition at page 17).

Referring to equation for capillary pressure $P_C$ given above, in some embodiments, it may be desirable to select a capillary array material that will generate a relatively small contact angle $\theta$ when wetted by a sample in order to increase the capillary pressure $P_C$. In order to minimize the contact angle $\theta$, it may be desirable to select a material for capillary array 16 that exhibits a surface energy that substantially matches or exceeds the surface tension of the sample. The contact angle $\theta$ may be minimized when the surface energy of the capillary array material is substantially equal to or greater than the surface tension of the sample. In some cases, it may also be desirable to select the capillaries such that the capillary constant a is small. For example, the capillary constant a for a columnar capillary is typically equal to $(rh)^{1/2}$, where r is a radius of the capillary. Thus, it may be desirable to minimize the radius r of that columnar capillary to increase the capillary pressure $P_C$ for a columnar capillary.

In some embodiments, capillary array 16 is formed of a material having a surface energy in a range of about 20 dynes/centimeter (dyn/cm) to about 82 dyn/cm, such as about 45 dyn/cm to about 72 dyn/cm. In some embodiments, the material for capillary array 16 is selected to have a surface energy close to that of water, or about 72 dyn/cm. A sample may be easier to remove from capillary array 16 compared to a conventional medical swab that includes a fibrous tip because the sample is held within capillary array 16 by surface energy, rather than absorption, as is the case with some conventional medical swabs. That is, less energy may be required to remove sample particles from capillary array 16. In some cases, a large percentage of sample particles are removed from capillary array 16 without the aid of a machine vortexer, although a machine vortexer may be utilized to help elute the sample from capillary array 16.

In general, capillary array 16 is comprised of a material that achieves the desired sample acquisition characteristics, which may depend upon the type of sample acquired (e.g., a sample from a wound may include a large quantity of water). In some embodiments, capillary array 16 is essentially non-absorbent or non-absorbent with respect to the sample with which capillary array 16 is used to acquire. As previously described, other material properties that may affect the ability of capillary array 16 to acquire and retain a sample include, but are not limited to, surface energy and affinity. For example, as described above, the material may be selected to have a particular surface energy in order to draw sample particles into the capillary defined by capillary array 16 by capillary force. Other sample acquisition characteristics may include substantial inertness relative to the sample or a relatively low rate of elution of chemicals or other contaminants that may affect a sample analysis process, e.g., when the sample is released from capillary array 16.

In some embodiments, capillary array 16 may include a base material that does not necessarily include the desired sample acquisition characteristics, and an external layer (e.g., a coating) comprising a material that affords hydrophilic, hydrophobic, positively-charged or negatively-charged surfaces to achieve the desired sample acquisition characteristics. For example, an inorganic coating (e.g., a silica coating) or an organic coating (e.g., polymeric coatings, such as polyacrylate) may afford hydrophilic characteristics to capillary array 16. Surface energy (or surface tension) characteristics of a material forming capillary array 16 may also be achieved with the aid of physical treatments, such as, but not limited to, corona treating in which the material being treated is exposed to an electrical discharge, or corona, electron beam treatments.

In some embodiments, the material may be selected such that capillary array 16 exhibits some compliancy (v. rigidity) relative to the sample source. This may help minimize damage to the sample source and reduce irritation on live samples. For example, capillary array 16 may be formed at least in part of nylon or a polymer, such as polysulfone, polycarbonate or a more compliant polymer, such as silicone. Example materials for capillary array 16 include, but are not limited to, any thermoplastic materials suitable for casting, profile extrusion, molding (e.g., injection molding) or embossing including, for example, polyolefins, polyesters, polyamides, poly(vinyl chloride), polymethyl methacrylate, polycarbonate, nylon, and the like. In other embodiments, capillary array 16 may be formed by defining a sheet of suitable material or fibers of the material into the desired capillary array structure.

In the embodiments described herein, capillary array 16 defines a major sample acquisition surface 22 that is oriented substantially perpendicular to longitudinal axis 24 of stem 12. In some embodiments, sample acquisition surface 22 has an area of about $0.1 \text{ cm}^2$ to about $1.5 \text{ cm}^2$, such as about $0.33 \text{ cm}^2$ to about $1.0 \text{ cm}^2$. In some embodiments, major sample acquisition surface 22 is not substantially planar. However, major sample acquisition surface 22 may still be oriented such that it is substantially perpendicular to longitudinal axis 24 of stem 12, as opposed to substantially parallel to axis 24. In general, sample acquisition surface 22 of each of the capillary arrays 16 described herein are oriented such that a user may position longitudinal axis 24 of stem 12 substantially perpendicular to a sample source surface in order to place at least a part of sample acquisition surface 22 of capillary array 16 in contact with the sample source. In some embodiments, the user may position longitudinal axis 24 of stem 12 substantially perpendicular to a sample source surface in order to place all or a majority of sample acquisition surface 22 of capillary array 16 in contact with the sample source. In some embodiments, major sample acquisition surface 22 may be positioned at angle J of about 60 degrees (°) to about 120°, such as about 75° to about 105° or about 90°, relative to major axis 24, where angle A may be measured in any direction relative to axis 24.

As shown in FIG. 1, capillary array 16 defines a plurality of sample acquisition channels 26 that acquire and retain a sample by capillary action. Thus, channels 26 may be referred to as "capillary channels." Capillary channels 26 are exposed (i.e., define an opening) along a sample acquisition surface 22 of capillary array 16 such that when at least a portion of sample acquisition surface 22 is placed in contact with a sample source, sample may be acquired by capillary channels 26 and retained within capillary array 16. In the embodiment shown in FIGS. 1-4, capillary channels 26 are defined between adjacent walls, where the walls extend substantially parallel to a major axis 24 of stem 12.

As shown in FIGS. 1-4, capillary channels 26 may be in fluidic communication with each other in some embodiments. For example, as shown in FIG. 2, a side of capillary array 16 that is substantially opposite sample acquisition surface 22 includes a plurality of distribution channels 36 that interconnect capillary channels 26. Distribution channels 36 of capillary array 16 help distribute a sample throughout the capillary array 16. The fluid may flow through distribution channels 36 by capillary action. In this way, distribution channels 36 fluidically couple different regions of capillary array 16, thereby resulting in a common capillary, i.e., a common region in which a sample may be retained.

Sample distribution capillaries 36 enable a user to orient sample acquisition surface 22 relative to the sample source in a wide range of angles in order to acquire the same. For example, if sample acquisition surface 22 is oriented such that only part of sample acquisition surface 22 is in contact with a sample source comprising a liquid sample, distribution capillaries 36 may help distribute the liquid sample across capillary array 16. Without distribution capillaries 36, the sample may only be retained within the portion of acquisition channels 26 proximate to the part of sample acquisition surface 22 in contact with the sample source.

In addition, a discontinuous surface defined by the distribution channels 36 may also help reduce the amount of material that is used to form capillary array 16 and decrease the rigidity of capillary array 16 such that capillary array 16 may exhibit some compliancy. A compliant capillary array 16 may be desirable in some cases to allow sample acquisition surface 22 to conform to a contour of a sample source surface, thereby enabling a larger percentage of sample acquisition surface 22 to contact the sample source without rocking or otherwise moving capillary array 16 relative to the sample source. In addition, an ability to of surface 22 to generally conform to a contour of a sample source surface may help minimize damage to the sample source when capillary array 16 is placed in contact with the sample source.

As described in further detail below, stem 12 defines an inner lumen. A fluid may be introduced into stem 12, e.g., at proximal end 12A (FIG. 1), in order to release an acquired sample from capillary array 16. Flow distributor 20 helps distribute fluid from stem 12 across capillary array 16 in order to help elute a sample from a large portion of capillary channels 26. In FIGS. 1 and 2, capillary array 16 defines a sample acquisition surface 22 that is substantially larger in dimension than the diameter of stem 12. Thus, without flow distributor 20, fluid flowing from stem 12 to head 14 may only flow through a portion of capillary array 16, which may result in an ineffective elution of the sample from capillary array 16. Flow distributor 20 is configured to fit within holding member 18. In the embodiment shown in FIG. 2, a dimension $A_1$ of flow distributor 20 is substantially equal to dimension $A_2$ of sample acquisition surface 22 of capillary array 16. In some embodiments, flow distributor 20 comprises a membrane formed at least in part of nylon, polycarbonate, polytetrafluoroethylene (PTFE), polyvinylidene difluoride (PVDF) or any combinations thereof.

Sample acquisition device 10 may provide advantages over conventional medical swabs that are often used to acquire a sample from a source for further analysis. Conventional medical swabs typically include a fibrous non-woven (e.g., rayon or cotton) tip in a teardrop or ellipsoidal shape at one end of a stem. Typically, a user manually grasps the stem of the medical swab and places the fibrous tip in contact with the select tissue cells or other specimen to be obtained, e.g., from within a wound, ear, nose or throat of a human patient. Some of the targeted specimen adheres to the fibrous swab tip.

The conventional tip of the swab typically has a relatively large ratio of a sample acquisition surface area to volume held by the swab, thereby increasing the possibility of the specimen binding to the swab tip. The sample particles may be more difficult to release from the fibrous tip of a conventional swab when the specimen binds to the fibrous tip, thereby increasing the risk that acquired sample particles may be unavailable for sample analysis.

Variability in the composition of the nonwoven material of the fibrous swab tip, which may result from the type of nonwoven material and the construction of the swab, as well as variability in the user technique employed to acquire the sample may affect the quantity of sample that adheres to the swab tip. For example, depending on the user or the particular batch of swabs used to acquire a sample, the quantity of sample acquired by two different swabs may differ. As one example, some users may only place one part of the fibrous tip in contact with the sample source, while other users may move the swab around to expose more than one region of the fibrous tip in contact with the same source. Differences in sample acquisition techniques may result in the latter type of users acquiring a greater sample volume compared to the users that only place on part of the fibrous tip in contact with the sample source. The variance in sample size may affect the quality of sample analysis. Some sample analysis techniques may provide different results if the quantity of sample falls outside of an acceptable range, i.e., the sample volume is too large or too small. Thus, sample acquisition by conventional swabs may adversely affect some sample analysis techniques.

Sample acquisition device 10 is designed to minimize variability in acquired sample volume that may be attributable to different acquisition techniques (e.g., based on different users) or different batches of devices. As previously described, capillary array 16 of sample acquisition device 10 is designed to acquire a substantially fixed quantity of a sample from a sample source. Capillary array 16 is designed to hold a maximum volume of a sample, which may meter the volume of sample a user acquires. Some detection techniques that provide different results based on the quantity of sample analyzed, thus, it may be desirable to acquire a particular sample volume. In addition, in some embodiments, the material and structure of capillary array 16 may be selected to acquire the sample from a sample source in a relatively short amount of time, such as about two seconds to about ten seconds or about five seconds. In addition, distribution capillaries 36 help to distribute a sample throughout acquisition channels 26 in a time efficient manner, which also helps decrease the time required to acquire a sample with capillary array 16. A relatively short sample acquisition time helps minimize the possibility that a user will acquire an insufficient sample volume. That is, because capillary array 16 will begin acquiring a sample from a sample source via capillary force once capillary array 16 is engaged with the source, reliance on user skill to acquire a sufficient volume of sample is minimized.

In the embodiment shown in FIGS. 1 and 2, the orientation of sample acquisition sample acquisition surface 22 relative to longitudinal axis 24 of stem 12 may help minimize variability in acquired sample volume that is attributable to user technique. For example, it may be easier for a user to place sample acquisition surface 22 in contact with a sample source compared to a conventional swab or another device that includes a major sample acquisition surface that is substantially parallel to the longitudinal axis of the swab stem. In the case of a conventional swab, the user may have to turn the swab stem at different angles relative to the sample source in order to place the various surfaces of the fibrous tip in contact with the sample source. The configuration of the swab, which defines a sample acquisition surface in many different planes, may result in operator error during the sample acquisition process. For example, a quantity of sample acquired by a particular swab design may differ depending upon the particular user or the particular sample source. In addition, the manipulation of the fibrous tip of the conventional medical relative to the sample source may result in inconsistent sample source sizes between users, or even between different trials of the same user.

In the embodiment of sample acquisition device 10 shown in FIGS. 1 and 2, on the other hand, user may hold stem 12 of sample acquisition device 10 in one orientation relative to the sample source in order to place substantially all of sample acquisition surface 22 in contact with the sample source. Thus, the acquired sample size may be substantially uniform, despite different users or different types of sample sources because the orientation of sample acquisition surface 22 is simplified compared to a conventional swab.

Sample acquisition device 10 also helps define the size of the sample source region from which a sample is acquired. In particular, capillary array 16 draws in the sample based on the contact between sample acquisition surface 22 and the sample source. Accordingly, in order to acquire the sample, the user does not need to move sample acquisition device 10 relative to the sample source, and may instead hold sample acquisition device 10 in a single region of the sample source. In some embodiments, however, the user may rotate capillary array 16 relative to the sample source or move capillary array 16 relative to the sample source. Thus, in some embodiments, the size of the portion of the sample source from which the sample is acquired is defined by the size of sample acquisition surface 22. In contrast, a fibrous tip of a conventional medical swab includes multiple surfaces with which a sample may be acquired, and, accordingly, the user typically determines the size of the region of the sample source from which a sample is acquired. This may lead to inconsistencies of in the size of the sample source region based on the particular user taking the sample.

Some users may be inclined to place outer surface 18A (FIG. 2) of holding member 18 in contact with a sample source. In the embodiment shown in FIGS. 1 and 2, outer surface 18A of holding member 18 does not include a capillary array, and any sample incidentally acquired by outer surface 18A may not be used for sample analysis. In some embodiments, in order to discourage placing outer surface 18A of holding member 18 in contact with a same source, outer surface 18A may be appear to be relatively smooth, thereby indicating to a user that a sample would not easily be acquired or retained by outer surface 18A. This may indicate to the user that it is most likely not the intended use of sample acquisition device to acquire a sample via outer surface 18A of holding member 18. The smooth outer surface 18A may be designed such that it is not possible for a sample to adsorb to outer surface 18A.

In some embodiments, such as embodiments in which capillary array 16 is manufactured by an injection molding process, variance in capillary array 16 size between different batches of sample acquisition devices 10 may be minimized, thereby minimizing variance in sample volume that may be attributable to the batch of sample acquisition devices 10. In addition, due to the structure of capillary array 16 and the material that may be used to form capillary array 16, the quantity of chemicals that may contaminate or interfere with the analysis of the acquired sample may be minimized in some embodiments, such as embodiments in which capillary array 16 is comprised of a polymer or steel. On the other hand, the fibrous tip of medical swabs may include chemicals transfer to the sample when the sample is eluted from the swab. These chemicals may contaminate or interfere with the analysis of the sample. For example, some fibrous swab tips may include various adhesives (e.g., to adhere the fibrous material to a stem), binders, surfactants, processing aids, and soluble oligomers that may interfere with a detection technique.

Depending upon the construction of the conventional medical swab, fibers from the fibrous tip may transfer to the sample source, which may be undesirable. For example, in the case of an open wound in a human patient, transfer of fibers from the conventional medical swab to the open wound may agitate the wound, and in some cases, encourage infection of the wound. As another example, contaminating a food preparation surface with fibers may increase the risk of transferring fibers to food placed on the surface. Capillary array 16 is formed of a material that exhibits fewer transferable particles compared to a fibrous tip of a conventional swab, and, accordingly, the possibility of the material of capillary array 16 contaminating a sample source or a sample is decreased when a sample is acquired via sample acquisition device compared to a conventional swab including a fibrous tip, e.g., a rayon or cotton tip.

Figure 3:
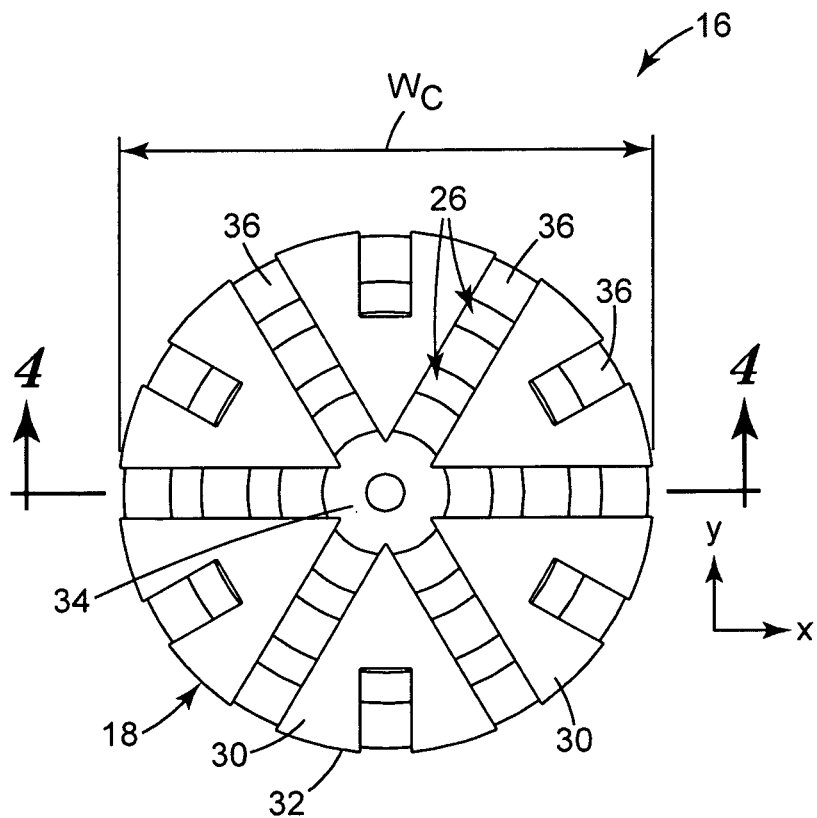
FIG. 3 is a plan view of the sample distribution surface of the capillary array of FIG. 2.
Figure 4:
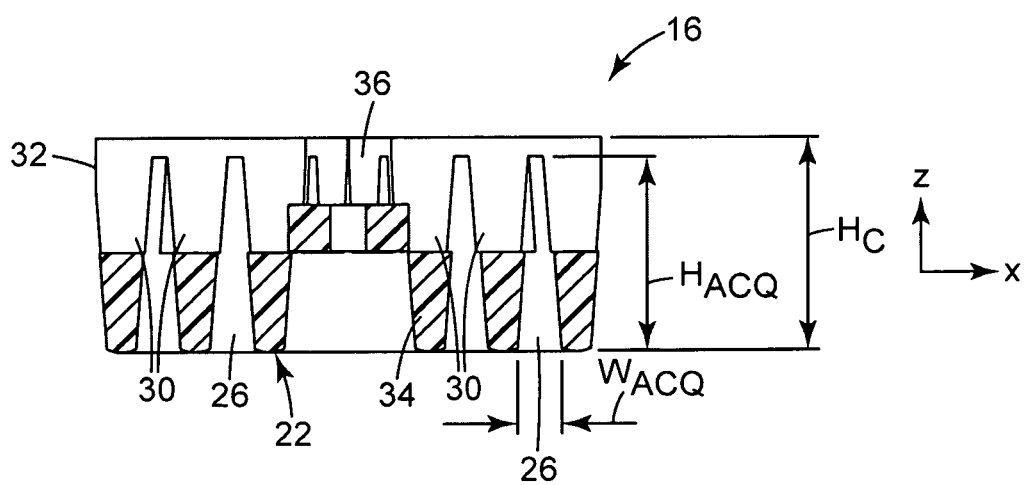
FIG. 4 is a schematic cross-sectional view of the capillary array of FIG. 2 taken along line 4-4 in FIG. 2.

FIG. 3 is a plan view of capillary array 16 of sample acquisition device 10, and illustrates a surface of capillary array 16 substantially opposite sample acquisition surface 22. FIG. 4 is a side view of capillary array 16 taken along line 4-4 in FIG. 3. As illustrated in FIGS. 3 and 4, structures 30 and wall 32 of holding member 18 define a plurality of distribution channels 36 that are in fluid communication with each other and fluidically couple capillary channels 26. A fluid, such as a liquid or air, or sample particles may flow between capillary channels 26 via distribution channels 36. Structures 34 define sample acquisition channels 26 that acquire and retain a sample by capillary action. In the embodiment shown in FIGS. 3-4, structures 34 are substantially concentric circles, thereby defining a plurality of substantially concentric channels 26. In some embodiments, structures 30 and 34 may be integral. In other embodiments, structures 30 and 34 may be separate structures that are mechanically coupled together, e.g., with the aid of an adhesive, interlocking parts or ultrasonic welding. In the embodiment shown in FIG. 4, structures 34 define substantially rounded edges along sample acquisition surface 22 in order to minimize abrasiveness to a sample source. However, in other embodiments, structures 34 may define sharp edges.

Capillary array 16 may be configured to hold a predetermined volume of a sample by selecting the size of capillary channels 26 and distribution channels 36. The configuration of structures 30, 34 may be used to modify the size of acquisition channels 26 and distribution channels 36, i.e., the total volume of channels 26, 36. In one embodiment, capillary array 16 is configured to hold between about 50 microliters (μL) and about 200 μL of a sample. In general, once capillary array 16 is "full," i.e., has drawn in as much sample as possible, capillary array 16 typically cannot receive any further quantity of samples. In some embodiments in which stem 12 is in fluidic communication with capillary array 16, stem 12 may include a vent hole that helps capillary channels 26 draw in a sample by capillary force. The vent hole may enable fluid to enter acquisition channels 26 and distribution channels 36 by releasing back pressure in channels 26, 36 through stem 12.

In general, it is believed that as a width $W_{ACQ}$ of sample acquisition channels 26 decrease, the sample acquisition time decreases. Thus, a narrower capillary channel width $W_{ACQ}$ may increase the speed of sample acquisition. Both the height $H_{ACQ}$ of sample acquisition channels 26 and an area of sample acquisition surface 22 may be selected to achieve a particular sample volume capacity. In the embodiment shown in FIGS. 1-4, the height (or "depth") $H_{ACQ}$ of sample acquisition channels 26 is generally measured in a direction generally perpendicular to sample acquisition surface 22. It is believed that as the height $H_{ACQ}$ of channels 26 increases, the speed at which capillary array 16 may capture a sample decreases. In addition, as an area of sample acquisition surface 22 increases, a possibility of non-specific binding of the sample to capillary array 16 may also increase. Sample particles that bind to surfaces of capillary array 16, rather than being drawn into capillary channels 26 and distribution channels 36 by adsorption, may not be easily released from capillary array 16. Accordingly, sample particles that bind to capillary array 16 may not be available for a sample analysis technique. Thus, the size of channels 26, 36 and the area of sample acquisition surface 22 may be balanced in order to arrive at a capillary array 16 that acquires a useful sample volume sample within a useful time range and without substantial binding of the sample particles to sample acquisition surface 22.

In some embodiments, sample acquisition channels 26 each have a greatest width $W_{ACQ}$ along sample acquisition surface 22 of about 0.25 mm to about 1.5 mm, such as about 0.5 mm to about 1 mm, and a greatest height $H_{ACQ}$ of about 0.1 mm to about 15 mm, such as about 5 mm to about 10 mm, which may result in a capillary array 16 that is configured to acquire and retain a maximum sample volume about 100 μL in less than about 2 seconds using a relatively hydrophilic polymer, such as polycarbonate, and an aqueous fluid of about 1 centipoise (cp).

In the embodiment shown in FIGS. 1-4, capillary array 16 has a relatively large surface area 22, thus maximizing the contact area with the sample source. Capillary array 16 has a large contact area in comparison to the height $H_{ACQ}$ of capillary channels 26. In some embodiments, capillary array 16 has a two-dimensional aspect ratio of about 3:1 to about 100:1, where the ratio is a ratio of a greatest dimension of a capillary channel 26 along the x-axis or y-axis, or substantially along the x-y plane (orthogonal x-y-z axes are shown in FIGS. 3 and 4) to the greatest dimension of the capillary channel 26 substantially along the z-axis or substantially along the x-z plane. Thus, in some embodiments, capillary array 16 has a larger sample acquisition surface area 22 than height $H_{ACQ}$ of sample acquisition channels 26.

In one embodiment, sample acquisition surface 22 may have a greatest width Wc of about 1 millimeter (mm) to about 20 mm, such as about 5 mm to about 10 mm. In the embodiment shown in FIGS. 3-4, the greatest width $W_C$ of capillary array 16 may also be referred to as a diameter of capillary array 16. However, in some embodiments, capillary array 16 does not have a circular cross-section along the sample acquisition surface 22, and, therefore may not have a diameter. In one embodiment, capillary array 16 has a greatest height $H_C$ of about 0.5 cm to about 20 cm, such as about 2.5 cm to about 5 cm. However, the height $H_C$ of capillary array 16 may be any suitable value. In the embodiment shown in FIGS. 1-4, height $H_C$ of capillary array 16 is greater than height $H_{ACQ}$ of acquisition channels 26.

The dimensions of capillary array 16 and channels 26, 36 provided above are merely examples of some embodiments. The size and configuration of capillary array 16 and channels 26, 36 may be modified to achieve different capillary array volumes, as well as different wicking times for drawing a substance of a particular viscosity into common capillary channels 26. For example, the dimensions channels 26, 36, as well as sample acquisition surface 22 of capillary array 16, may be modified to accommodate the desired maximum sample value. In one embodiment, capillary array 16 is engineered to draw in an aqueous sample volume of about 240 μL to about 350 μL in about 5 seconds, where the sample has a viscosity of about 100 cp.

A surface energy of the material with which capillary array 16 is constructed relative to a surface energy of the target sample may affect the volume of sample acquired by capillary array 16, as well as the total time required to draw the sample into capillary array 16. The relative surface energies, however, may also affect the release property of capillary array 16, i.e., the ease at which the sample may be released from capillary array 16. In general, the greater the surface energy of the material forming capillary array 16 compared to the surface energy of the sample, the greater the adhesion between the sample and capillary array 16. However, the greater the adhesion between the sample and capillary array 16, the more difficult it is to release the sample from capillary array 16. Thus, the ability of capillary array 16 to retain the sample and release the sample is balanced. As described above, in some embodiments, capillary array 16 is formed of a material having a surface energy in a range of about 20 dyn/cm to about 82 dyn/cm, such as about 45 dyn/cm to about 72 dyn/cm. In some embodiments, the material for capillary array 16 is selected to have a surface energy close to that of water, or about 72 dyn/cm.

Capillary channels 26 and distribution channels 36 are interconnected to define a common capillary for receiving and retaining a sample. Sample release from capillary array 16 that defines a common capillary may also be easier compared to a sample acquisition device that defines a plurality of separate capillaries that are not in fluid communication because there are fewer surfaces to which the sample may adhere.

It may be desirable to minimize a ratio of the area of sample acquisition surface 22 to volume of sample retained by capillary array 16 ("surface area to volume ratio"). In some cases, it is believed that smaller surface area to volume ratio may also result in a capillary array increase the ability of capillary array 16 to retain the sample, e.g., without dripping. In addition, in some cases, it is desirable to minimize the surface area to volume ratio of capillary array 16 in order to minimize the possibility of sample particles binding to the material of capillary array 16. Sample particles that bind to capillary array 16, rather than being drawn into capillary array 16 by adsorption, may not be easily released from capillary array 16. Accordingly, sample particles that bind to sample contact surfaces of capillary array 16 may not be available for a sample analysis technique.

The surface area to volume ratio as well as the material for capillary array 16 may be selected to achieve a better consistency between the amount of sample particles obtained via capillary array 16 and the amount of sample particles released from capillary array 16. In order to minimize physical binding between sample particles and sample contact surfaces of capillary array 16, capillary array 16 may be constructed of a material that reduces entrapment of sample particles. With some types of sample particles, such as particles from a wound of a human patient, there is less entrapment of sample particles with smoother material, e.g., a material that may define a surface with minimal protrusions or other inconsistencies. In some embodiments in which sample acquisition device 10 is use to acquire a biological sample from a wound of a human patient, capillary array 16 may be formed at least in part of polysulfone or polycarbonate in order to further help minimize binding between sample particles and surfaces of capillary array 16.

As previously described, a sample retained by capillary array 16 may be subsequently analyzed for detection of a particular microorganism or another sample analysis process. In some cases, the sample is combined with a reagent for a subsequent sample preparation or analysis process. In some embodiments, capillary array 16 may include one or more reagents or other chemicals that are used in a subsequent sample preparation or analysis process. For example, the reagent may be coated or otherwise applied to structures 30 or otherwise within channels 26, 36. Thus, when the sample is drawn into channels 26, 36, the sample may begin reacting with the reagent.

In some embodiments, capillary array 16 may include a reagent such as, but are not limited to, a lysis reagent (e.g., lysostaphin, lysozyme, mutanolysin or other enzymes), a protein-digesting reagent, a nucleic acid amplifying enzyme, an oligonucleotide, a probe, nucleotide triphosphates, a buffer, a salt, a surfactant, a dye, a nucleic acid control, a nucleic acid amplifying enzyme, a reducing agent, dimethyl sulfoxide (DMSO), glycerol, ethylenediaminetetraacetic acid (EDTA), ethylene glycol-bis(2-aminoethylether)-N,N,N',N'-tetraacetic acid (EGTA), microspheres capable of binding a nucleic acid, and a combination thereof. In addition, in some embodiments, the reagent is selected from a group including RNase, DNase, an RNase inhibitor, a DNase inhibitor, Bovine Serum Albumin, spermidine, and a preservative. Other reagents may include salts, buffers that regulate the pH of reaction media involved in the sample analysis or preparation, dyes, detergents or surfactants that lyse or de-clump cells, improve mixing or enhance fluid flow.

One factor to consider when designing capillary array 16 includes the manufacturability of capillary array 16. In some embodiments, capillary array 16 may be formed by a molding technique, such as injection molding, compression molding, extrusion molding, and the like. Another factor that may be considered when designing the configuration of capillary array 16 includes a ratio of the surface area of sample contact surfaces of capillary array 16 to the total volume retained by channels 26, 36.

The material and design of capillary array 16 may also be selected to achieve sufficient sample release from capillary array 16. For example, it may be undesirable to design capillary array 16 to include features that are so small that sample particles may become trapped in the features or features that include rough surfaces that bind to the sample particles. Capillary array 16 may also be comprised of a material that does not substantially react with the sample and does not substantially release contaminants that may interfere with the sample analysis technique employed to analyze the sample.

FIGS. 5A-5C illustrate a technique for acquiring a sample 42 with sample acquisition device 10 from a wound 40 and releasing the sample 42 from sample acquisition device 10. While wound 40 is primarily referred to throughout the remainder of the disclosure, in other embodiments, sample acquisition devices described herein may acquire a sample from any suitable living or nonliving sample source.

Wound 40 may be cleaned, e.g., with saline, prior to obtaining the sample in order to acquire a sample that is more representative of the wound tissue bioburden than surface contamination. Minimizing or eliminating surface contaminants helps acquire a sample that provides more clinically meaningful information.

As shown in FIG. 5A, in one technique, a user may place capillary array 16 in contact with wound 40, e.g., while directly or indirectly holding stem 12. With the embodiment of capillary array 16 shown in FIG. 5A, which includes a major sample acquisition surface 22 that is oriented substantially perpendicular to major axis 24 of stem 12, major axis 24 of stem 12 may be oriented substantially orthogonally to a major surface of wound 40 when major sample acquisition surface 22 is engaged with wound 40. Wound 40 may be located on a surface of a patient that is not substantially planar, such as on an arm or leg. Accordingly, the major surface of wound 40 may not be substantially planar. However, stem 12 may be generally oriented at an angle of about 60° to about 120° relative to the major surface of the wound in order to engage major sample acquisition surface 22 with wound 40.

Given the relatively small size of capillary array 16 compared to wound 40 and because wound 40 is not substantially rigid, but somewhat pliable, a user may place capillary array 16 into contact with wound 40 without substantial manipulation of sample acquisition device 10 relative to wound 40. For example, in some cases, the user may not pivot head 14 relative to wound 40 in order to place capillary array 16 into contact with wound 40 because of the configuration of stem 12 and head 14 of sample acquisition device 10.

In one embodiment, a user may acquire sample from wound 40 according to a modified quantitative swab sampling technique described by Levine et al. in "[t]he Quantitative Swab Culture and Smear: A Quick and Simple Method for Determining the Number of Viable Aerobic Bacteria on Open Wounds," the Journal of Trauma; 16 (2):89-94 (1976) ("Levine technique"). The Levine technique typically involves cleaning wound 40 with, e.g., sterile gauze and saline, identifying viable tissue within the wound for sampling, and direct application of a fibrous tip of a conventional swab over a 1 square centimeter ($cm^2$) area of a wound for about 5 seconds and with sufficient pressure to extract fluid from within the wound tissue. The tip of the conventional swab is typically smaller than 1 $cm^2$, and, accordingly, a user may rotate the conventional swab within the 1 $cm^2$ area. In addition, the user may rotate the swab in order to engage different surfaces of the fibrous swab tip with the sample source. As described above, in some embodiments, capillary array 16 of sample acquisition device 10 defines a sample acquisition surface 22 that is generally shaped and sized to cover the desired sample area for acquiring a useful sample. In one embodiment, sample acquisition surface 22 has an area of about 1 $cm^2$. In such an embodiment, sample acquisition device 10 eliminates the need for the user to rotate capillary array 16 over the 1 $cm^2$ area dictated by the Levine sample acquisition technique, thereby eliminating the need for the user to estimate the boundaries of the 1 $cm^2$ area.

As the user presses capillary array 16 into wound 40, as indicated by arrow 44, and holds capillary array 16 in contact with wound 40, sample 42 is expressed from wound 40. The use may apply pressure to wound 40 via capillary array 16 in order to express more exudate from wound 40. As sample acquisition device 10 is pressed into the wound and a fluid (or another sample composition) is produced from within wound 40, the fluid is adsorbed into capillary array 16 and held in capillary array 16 by capillary pressure. That is, capillary action draws sample 42, whether liquid, solid or a combination thereof, from wound 40 into capillary array 16. Sample 42 may include, for example, wound fluid (e.g., puss), as well as a sample of a bacteria or other microorganism that may be contaminating wound 40.

The material (and resulting surface energy) of capillary array 16 may be selected based on the viscosity of sample 42, which may vary based on whether sample 42 is liquid, solid or a combination thereof (e.g., any state between liquid and solid). In some cases, depending upon the particular design of capillary array 16, sample 42 may be better acquired by twirling head 14 and capillary array 16 relative to wound 40, as indicated by arrow 46. In other embodiments, however, capillary array 16 is held substantially in place relative to wound 40.

The user may hold capillary array 16 in contact with wound 40 for at least the minimum amount of time required to acquire a sufficient amount of sample 42 for a sample analysis process. As previously described, the material and design of capillary array 16 may be engineered to hold a predetermined amount of sample 42. For different sample analysis techniques, the desirable amount of sample 42 may differ. In some embodiments, capillary array 16 may be designed to hold a sample volume of about 0.025 milliliters (mL) to about 0.5 mL, such as about 0.05 mL to about 0.2 mL or about 0.1 mL. In some embodiments, capillary array 16 is designed to acquire a sample volume of about 0.025 mL to about 0.5 mL in less than about 15 seconds, such as about 5 seconds.

Rather than relying on a user to rotate a fibrous nonwoven tip of a conventional swab relative to wound 40 in order to acquire a sample, and make the subsequent judgment call of determining when a sufficient amount of sample has been retained on the conventional swab, sample acquisition device 10 is designed such that the user may hold capillary array 16 in contact with wound 40 for at least a minimum amount of time, which may be determined by the manufacturer of sample acquisition device 10. The predetermined amount of sample acquisition time may be selected to fill capillary array 16, i.e., such that capillary array 16 cannot hold any more sample 42. Furthermore, in some embodiments, capillary array 16 may be formed at least in part of a substantially transparent polymer, such that a sample retained within capillary array 16 is visible. In this way, the capillary array 16 may provide visual feedback relating to sample acquisition and a user may make a more informed judgment as to when enough sample has been acquired by viewing the sample retained with array 16.

Conventional swabs are designed such that one portion of the fibrous swab tip may become saturated with a sample before another portion, thereby requiring the user to make judgment calls as to when a portion of the swab tip is saturated, and, thereafter, moving the swab tip to wound 40 in order to acquire more sample in another region of the swab tip. Sample acquisition device 10 eliminates the need for such judgment calls as to when a particular region of a fibrous swab tip is saturated. In addition, sample acquisition device 10 eliminates the reliance on a user's skill to move the sample acquisition surface relative to wound 40 in order to acquire a sample. In addition, because capillary array 16 draws in sample 42 by capillary pressure, the need for user coordination to apply a suction force while pressing capillary array 16 against wound 40 in order to draw sample into array 16 is eliminated. As described below, however, in some embodiments, a sample acquisition device may rely on both a suction source and capillary action to obtain a sample.

As shown in FIG. 5B, after the user holds capillary array 16 in contact with wound 40 and sample 42 is retained within capillary array 16, the user may disengage sample acquisition device 10 from wound 40, as indicated by arrow 48. The entire sample acquisition device 10 or at least capillary array 16 may be placed in a storage container for storage or during transportation, or the sample can be immediately transferred to another container by washing the sample out of the acquisition device.

FIG. 5C illustrates one technique for releasing sample 42 from sample acquisition device 10. The user may submerge capillary array 16 in a wash solution 50 (e.g., a buffer or another release medium). In some cases, the user may agitate capillary array 16 within the wash solution 50 by in order to encourage the release of sample 42, such as by moving capillary array 16 around within wash solution 50. The adsorption of sample 42 by capillary array 16 enables the user to release a large percentage of sample particles from capillary array 16 with a relatively low amount of energy, e.g., with manual agitation of device 10 within solution 50. However, in some embodiments, sample 42 may be released from capillary array 16 with the aid of a vortexing machine. After sample 42 is released from capillary array 16, the user may conduct any suitable sample preparation and analysis technique using buffer 50 with sample 42.

In one embodiment, capillary array 16 is formed form a material, such as a polymer, that minimizes or eliminates the amount of wash solution 50 that capillary array 16 retains when at least partially submerged in wash solution 50. This may help maximize the amount of sample 42 that is released into wash solution 50 and increase the efficiency with which sample 42 is released from capillary array 16. In addition, the material for capillary array 16 may be selected to minimize the amount of additives or other materials released into wash solution 50. In the case of many conventional swabs, the fibers of the conventional swab bud may be coated with carboxy methyl cellulose (CMC) in order to help the fibers hold their bud-like structure. When the conventional swab bud is exposed to a wash solution, the CMC and other additives in the swab bud may be leached out into the wash solution. The CMC and other additives may impact a subsequent sample analysis technique. Capillary array 16 described herein helps minimize or even eliminate the exudates that are released from the sample acquisition device compared to a conventional swab bud.

Figures 6A, 6B:
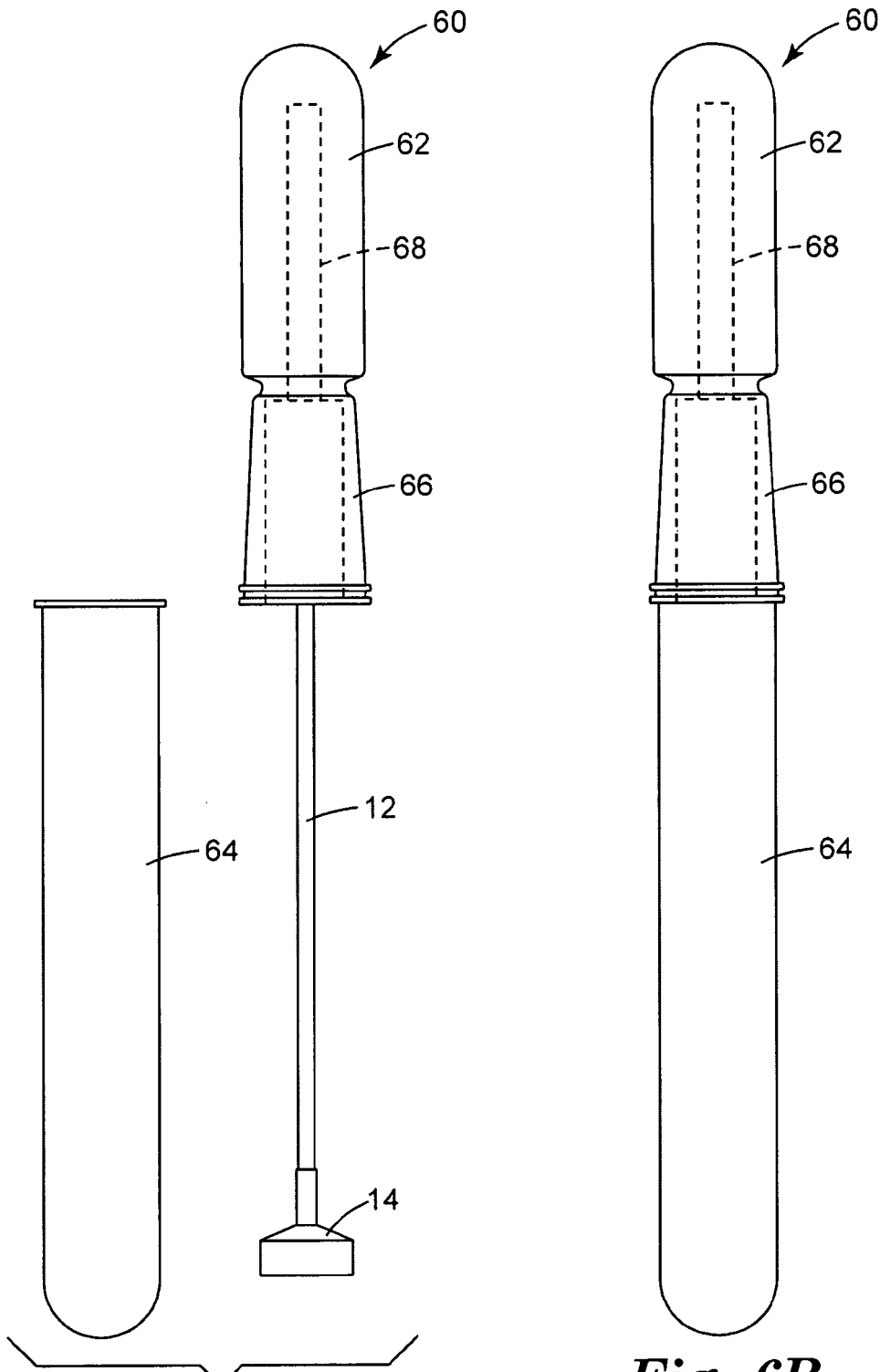
FIGS. 6A-6B illustrate another embodiment of a sample acquisition device (including the fluid storage capsule).

FIGS. 6A and 6B are schematic illustrations of another embodiment of sample acquisition device 60, which is similar to sample acquisition device 10 of FIGS. 1 and 2, but includes rinse fluid bulb 62, cap head 64, and cap base 66. Stem 12 defines an inner lumen (not shown in FIGS. 6A and 6B) that is fluidically coupled to capillary array 16 (not shown in FIGS. 6A and 6B). After a user acquire sample 42 from wound 40 with sample acquisition device 60 using techniques described above in FIG. 5A with respect to sample acquisition device 10, the user may cover head 14 with cap head 64 to help prevent contamination of sample 42. For example, cap head 64 and cap base 66 may be placed over stem 12 and head 14 during storage of sample acquisition device 10, as well as after sample 42 is acquired. In some embodiments, cap head 64 and cap base 66 may help keep stem 12 and head 14 sterile prior to use of sample acquisition device 60.

Cap head 64 is configured to removably connect to cap base 66, e.g., via interlocking components or a friction fit. In FIG. 6A, cap head 64 is placed over stem 12 and head 14, and coupled to cap base 66. In other embodiments, other types of covers may be used to protect the sample retained within capillary array 16 from contamination, as well as protect capillary array 16 from contamination prior to sample acquisition.

Bulb 62 is comprised of a flexible material that defines a container for retaining a rinse fluid 70, such as a buffer solution that does not react with sample 42. However, in some embodiments, the rinse fluid may include a reagent, such as the reagents described above with respect to capillary array 16. In one embodiment, bulb 62 stores a volume of rinse fluid 70 that is sufficient to elute substantially all of sample 42 from capillary array 16 (not shown in FIGS. 6A and 6B) as rinse fluid 70 flows through stem 12 and through capillary array 16. In the embodiment shown in FIGS. 6A and 6B, bulb 62 stores a volume of rinse fluid 70 that is about five times to about twenty times the maximum sample volume capillary array 16 is designed to retain. For example, bulb 62 may store a volume of rinse fluid 70 that is about ten times the maximum sample volume capillary array 16 is designed to retain. For example, bulb 62 may store a rinse fluid volume of about 0.1 mL to about 5 mL, such as about 0.5 mL to about 2 mL. In one embodiment, capillary array 16 is designed to hold a sample volume of about 0.1 mL and bulb 62 is configured to store a rinse fluid volume of about 1 mL.

Bulb 62 may include any suitable mechanism to retain rinse fluid 70 within bulb 62 until released by a user. In the embodiment shown in FIGS. 6A and 6B, snap valve 68 separates rinse fluid 70 from the inner lumen of stem 12. In other embodiments, sample acquisition device 60 may include another types of mechanical valve, laser valve or a membrane that may be ruptured by applying pressure to the membrane, e.g., by squeezing bulb 62.

Figure 7A:
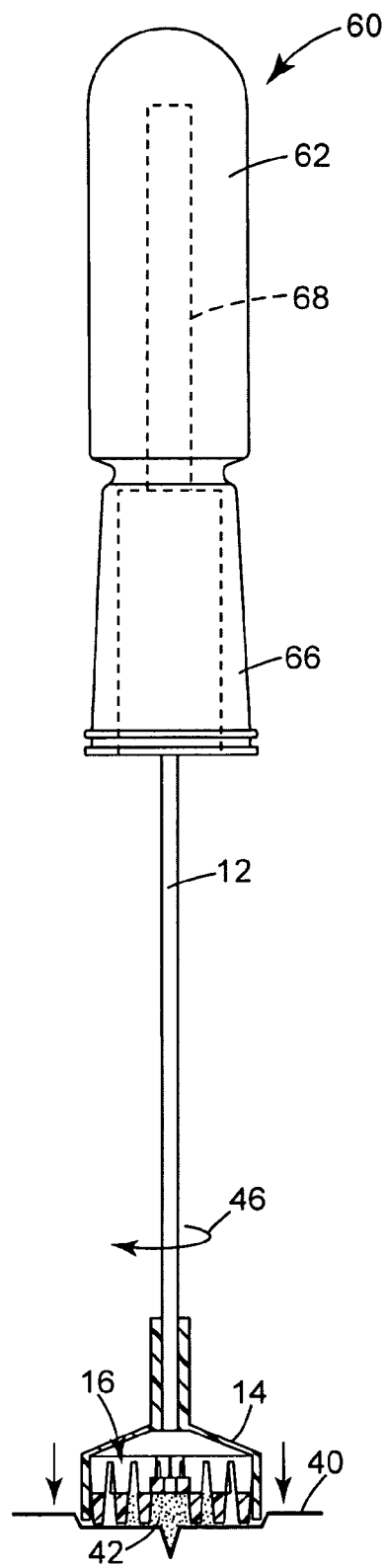
FIGS. 7A-7C illustrate a technique for acquiring a sample with the sample acquisition device of FIG. 1.
Figure 7B:
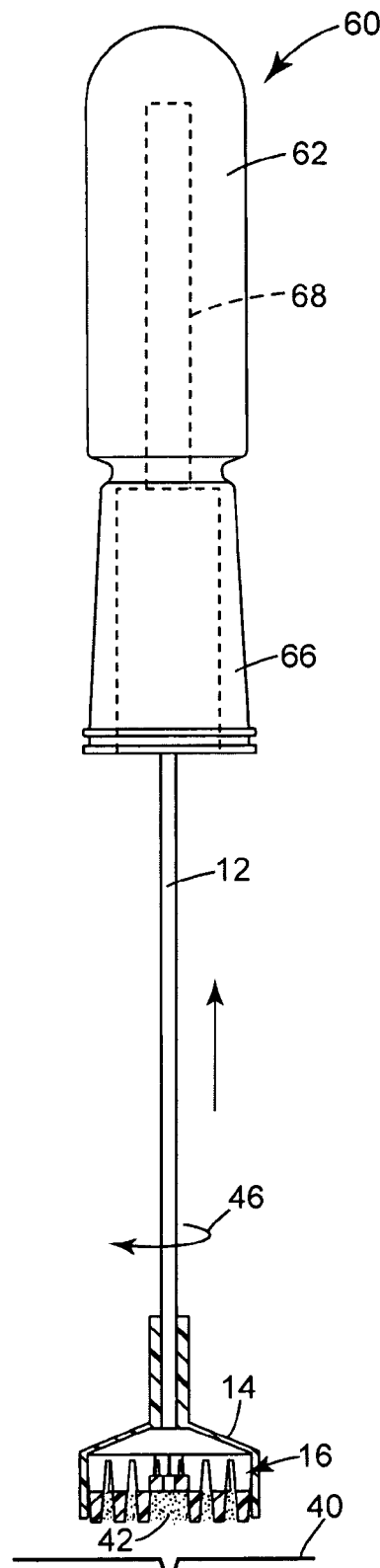
Figure 7C:
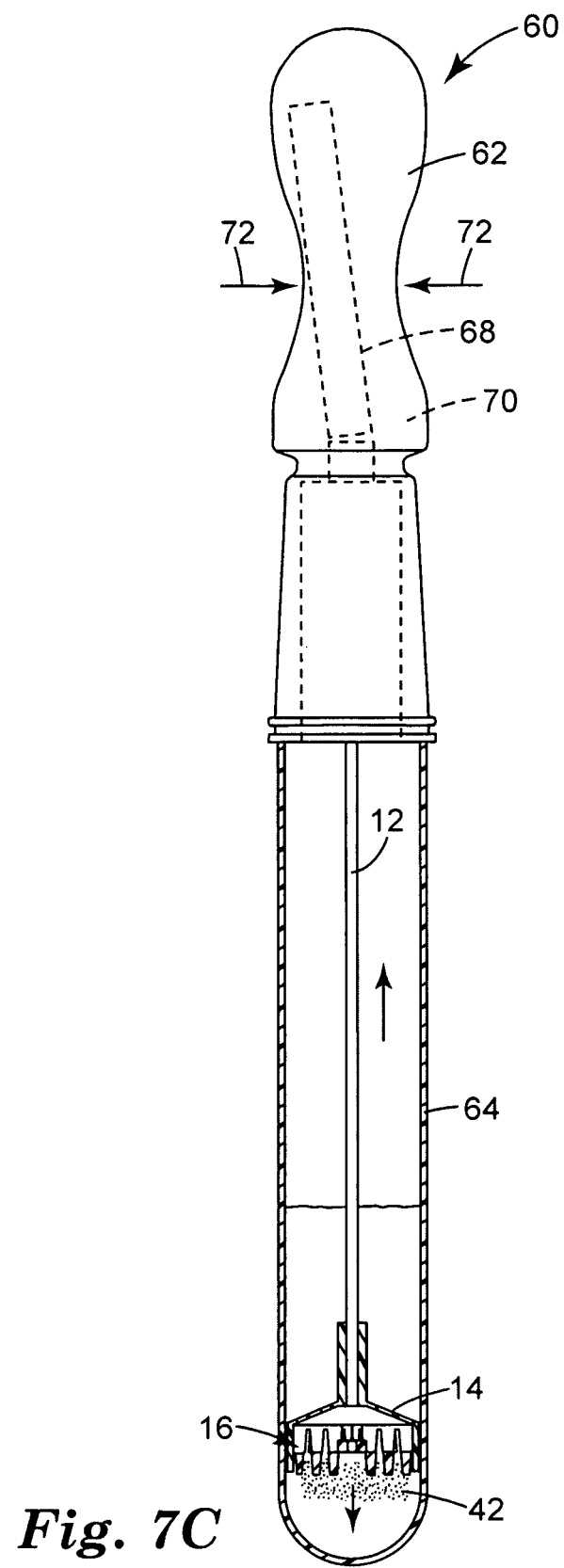

FIGS. 7A-7C illustrate an embodiment of a technique for acquiring a sample 42 from wound 40 with sample acquisition device 60 and releasing sample 42 from sample acquisition device 60. FIGS. 7A and 7B are similar to FIGS. 5A and 5B. In particular, a user may place capillary array 16 in contact with wound 40 in order to draw sample 42 into capillary array 16 by capillary action. The user may apply pressure to wound 40 by pressing capillary array 16 into wound 40 (while holding onto stem 12) in order to express more exudate from wound 40. After acquiring sample 42 from wound 40, the user may withdraw sample acquisition device 60 from the sample source (as shown in FIG. 7B) and cover head 14 with cap head 64 for storage (not shown). Head 14 may remain covered with cap head 64 until sample 42 is needed for sample preparation and analysis.

In order to elute sample 42 from capillary array 16, the user may release sample 42 from capillary array 16 by releasing rinse fluid 70 from bulb 62, e.g., by breaking snap valve 68. FIG. 7C illustrates an elution step, and illustrates snap valve 68 in a broken state, i.e., a state in which a fluid channel between bulb 62 and stem 12 is substantially open. Cap head 64 may act as a storage container for receiving the eluted sample 42 and rinse fluid 70. Thus, as shown in FIG. 7C, the user may cover head 14 of sample acquisition device 60 with cap head 64 prior to releasing rinse fluid 70 from bulb 62. Alternatively, the user may place head 14 of sample acquisition device 10 over another storage container prior to releasing rinse fluid 70. Upon breaking snap valve 68, rinse fluid 70 flows through stem 12 and through capillary array 16, sample 42 is released from capillary array 16 and into cap head 64 by the force of the flowing rinse fluid. In order to encourage the flow of rinse fluid 70 from bulb 62, the user may squeeze bulb 62, as generally indicated by arrows 72 in FIG. 7C. Squeezing bulb 62 may help increase the pressure through which rinse fluid 70 flows through stem 12 and capillary array 16, which may help increase the percentage of sample 42 that is eluted from capillary array 16.

In some cases, capillary array 16 may be designed such that the capillary action for drawing a sample into capillary array 16 is best achieved by maintaining capillary array 16 in a fixed position relative to the sample source. For example, in some embodiments, capillary array 16 may be designed such that capillary action may be adversely affected if a user twirls capillary array 16 relative to the sample source. Thus, in some embodiments, sample acquisition devices 10 or 60 may be designed to discourage twirling of head 14 relative to wound 40 or another sample source. For example, the handling end of stem 12 or the entire length of stem 12 may be shaped to be more flat than round in cross-section or include sharp edges that discourage twirling. If bulb 62 or another fluid chamber is coupled to stem 12, the bulb may also be shaped to be more flat than round in cross-section or include a sharp edge. Examples of shapes that are more flat than round in cross-section include, for example, ovals, rectangles, ellipses, and the like. Examples of shapes that include a sharp edge include, for example, triangles, squares, rectangles, other polygons, and the like. Other shapes are contemplated.

Figure 8A:
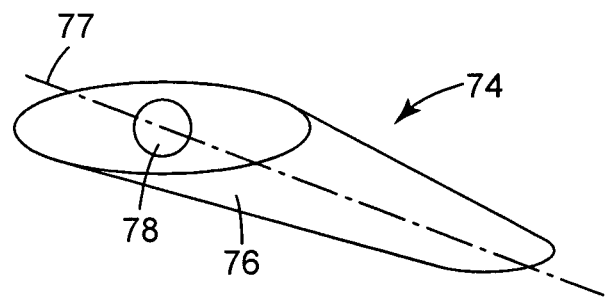
FIGS. 8A-8D illustrate embodiments of fluid delivery stems.

FIGS. 8A-8D illustrate different embodiments of stems 12. FIG. 8A illustrates stem 74, which includes body 76 defining inner lumen 78. Body 76 is configured to couple to capillary array 16, e.g., via an interference fit, adhesive, welding, and the like, either directly or indirectly. A cross-sectional shape of body 76 is selected to help discourage a user from rotating body 76 along center longitudinal axis 77, which runs substantially coaxial to a center axis of lumen 78. In the embodiment shown in FIG. 8A, body 76 has an elliptical or oval cross-sectional shape taken along a plane substantially perpendicular to longitudinal axis 77 of body 76.

A fluid source, such as bulb 62, may be coupled to an end of stem 74 substantially opposite the end on which capillary array 16 is coupled. Lumen 78 is configured to receive a fluid, such as a rinse fluid 70 (FIGS. 6A-7C). Capillary array 16 may be coupled to stem 74 such that it is in fluidic communication with lumen 78. In this way, fluid flowing through lumen 78 may also flow through capillary array 16 and elute any captured sample from capillary array 16. Because lumen 78 may not have the same width (i.e., measured along a plane substantially perpendicular to the longitudinal axis 77 of lumen 78) as capillary array 16, a flow distributor 20 (shown in FIG. 2) may help distribute the fluid flow across substantially all of the sample acquisition surface 22 of capillary array 16.

Figure 8B:
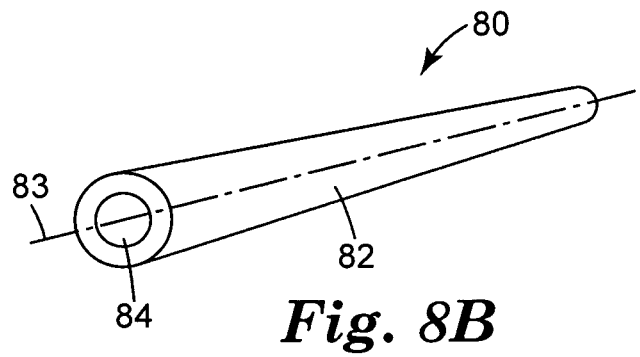

FIG. 8B illustrates stem 80, which includes body 82 defining inner lumen 84. Stem is substantially similar to stem 74 of FIG. 8B, but body 82 has a round cross-sectional shape, rather than a shape that discourages a user from rotating body 82 about a center longitudinal axis 83. Lumen 84 is similar to lumen 78 of FIG. 8A, and may fluidically couple a fluid source, such as bulb 62 (FIGS. 6A-7C) with capillary array 16.

Figure 8C:
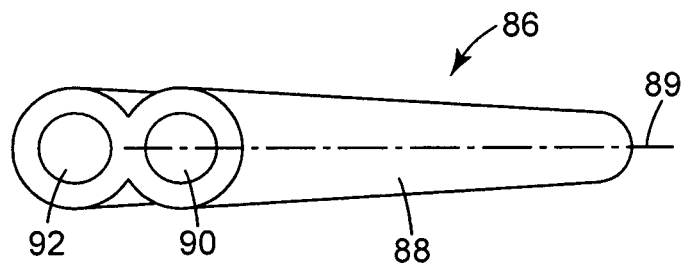

FIG. 8C illustrates stem 86, which includes body 88 defining adjacent lumens 90, 92. Just as with body 76 (FIG. 8A), body 88 is configured to couple to a capillary array 16 either directly or indirectly, e.g. with the aid of a holding member 18 (shown in FIG. 2). The non-circular cross-sectional shape of body 88 may help discourage a user from rotating body 88 about a longitudinal axis 89 when acquiring a sample. Lumens 90, 92 may couple to a common fluid source or separate fluid sources. Body 88 defining separate lumens 90, 92 may help define two different fluid delivery paths for two different types of fluid (e.g., a rinse fluid and a reagent or a rinse fluid and an air vent). Separate lumens 90, 92 within the body 76 may also help increase the volume of fluid that flows through stem 86 compared to stem 74 (FIG. 8A), which may help improve the percentage of sample that is eluted from an attached capillary array 16.

Figure 8D:
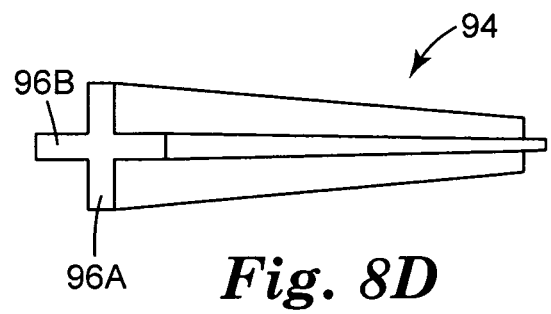

FIG. 8D illustrates stem 94, which includes body portions 96A, 96B. Unlike the stems shown in FIGS. 8A-8D, stem 94 does not include a lumen for receiving a fluid. Thus, stem 94 may be useful for a sample acquisition and elution technique shown in FIGS. 5A-5C, whereby capillary array 16 is at least partially submerged in a rinse fluid 50 in order to elute a sample from capillary array 16. Body portions 96A, 96B are merely one embodiment of a stem body that does not define a center lumen. Other stem body shapes and configurations are also contemplated. In the embodiment shown in FIG. 8D, body portions 96A, 96B are substantially equal in size. In other embodiments, body portions 96A, 96B may have different sizes.

Depending upon the particular type of sample source, it may be desirable for a user to apply a pressure when placing capillary array 16 in contact with the sample source in order to express more exudate from the source for acquisition by capillary array 16, as well as to engage a greater portion of major sample acquisition surface 22 in contact with the sample source. However, in the case of some sample sources, such as some open wounds 40 (FIGS. 5A-5C and 7A-7C), pressing capillary array 16 into contact with wound 40 may increase the risk of further agitating the wound. Thus, there may be a maximum desirable pressure in order to minimize further damage to a wound.

FIGS. 9A and 9B illustrate schematic plan views of an embodiment of a sample acquisition device 100 that includes a tactile feedback mechanism to indicate the relative pressure applied to a sample source by a user when engaging head 14 with the sample source. In particular, sample acquisition device 100 includes spring 102 and spring compression member 104. Sample acquisition device 100 also includes stem 12 and head 14, which includes capillary array 16 (not shown in FIGS. 9A and 9B). Spring 102 and spring compression member 104 are disposed around stem 12 such that spring 102 and compression member 104 may move relative to stem 12. In the embodiment shown in FIGS. 9A and 9B, spring 102 and compression member 104 are slidably mounted relative to stem 12. Any of the sample acquisition devices described herein may include the pressure feedback mechanism shown in FIGS. 9A and 9B.

Spring compression member 104 defines indentations 105 that are configured to engage with a user's fingers when a user is holding stem 12. For example, a user may grasp stem 12 by placing a thumb and index finger on opposite sides of compression member 104. The user may place capillary array 16 in contact with wound 40 (FIGS. 5A-5C and 7A-7C) while holding onto spring compression member 104. As the user presses capillary array 16 into wound 40, compression member 104 slides towards head 14, as indicated by arrow 106 in FIG. 9B, thereby compressing spring 102 against wall 108. A compressed spring 102 is shown in FIG. 9B. The compression of spring 102 provides a tactile feedback, as well as a visual feedback, that indicates the relative pressure that the user is applying to wound 40 via sample acquisition device 100. For example, the more pressure the user applies to wound 40 with sample acquisition device 100, the more spring 102 will compress. In other embodiments, a distal end 102A of spring 102 may be fixed via a technique other than wall 108, such as by adhering or otherwise attaching distal end 102A of spring 102 to stem 12.

In some embodiments, a spring constant of spring 102 may be selected to help regulate the amount of pressure that a user applies to wound 40. For example, a spring constant of spring 102 may be increased in order to increase the permissible pressure with which a user may apply to head 14 relative to wound 40. If spring 102 is fully compressed against wall 108, the pressure feedback mechanism of sample acquisition device 100 may indicate to the user that no further pressure should be applied to wound 40. However, while spring 102 indicates the relative amount of applied pressure, spring 102 may not prevent the user from applying further pressure.

FIGS. 10A and 10B illustrate a schematic perspective view of another embodiment of a sample acquisition device 110 that includes a tactile feedback mechanism to indicate relative pressure applied to a sample source. Sample acquisition device 110 includes stem 12 and head 112, which couples capillary array 114 to stem 12. Capillary array 114 may be similar to capillary array 16 (FIGS. 1-4) and defines one or more sample acquisition regions that draw in a predetermined maximum sample volume from wound 40 or another sample source via capillary action. However, capillary array 112 differs from capillary array 16 in that capillary array 114 extends past head 112 and is compressible and elastic, similar to a spring. Thus, as a user presses capillary array 114 into wound 40, capillary array 114 compresses (as shown in FIG. 10B), thereby providing the user with tactile feedback relating to the relative pressure with which capillary array 114 is pressed into wound 40. Capillary array 114 may be more complaint than a noncompressible capillary array 16, which may help provide a more gentle contact surface with a sample acquisition surface.

FIGS. 11A and 11B illustrate a schematic perspective view of another embodiment of a sample acquisition device 120 that includes a tactile feedback to indicate relative pressure applied to a sample source. Sample acquisition device 120 includes a stem 122 mechanically coupled to head 14 (schematically shown), which includes capillary array 16 (not shown in FIGS. 11A and 11B). Stem 122 comprises first stem portion 124 and second stem portion 126. First stem portion 124 is sized to at least partially fit within second stem portion 126 and is movable relative to second stem portion 126. In the embodiment shown in FIGS. 11A and 11B, second stem portion 126 defines an opening 127 configured to receive first portion 124. Thus, first and second stem portions 124, 126 have different dimensions along the x-axis direction, where orthogonal x-z axes are shown in FIG. 11A. First stem portion 124 may include a mechanism to prevent first stem portion 124 from being inadvertently removed from second stem portion 124. In other embodiments, second stem portion 126 may be configured to fit within first stem portion 124.

Sample acquisition device 120 also includes spring 128 (shown in phantom lines in FIGS. 11A and 11B), which is disposed within second stem portion 126. First stem portion 124 contacts spring 128, which is engaged with a substantially fixed wall 130 (shown in phantom lines in FIGS. 11A and 11B). In some embodiments, first stem portion 124 is directly or indirectly attached to spring 128, while in other embodiments, spring 128 and first stem portion 124 are unattached.

In order to acquire sample 42 from wound 40, a user may hold onto first portion 124 of stem 122 and position capillary array 16 (disposed within head 14) in contact with wound 40. After capillary array 16 is engaged with wound 40, the user may continue applying pressure to wound 40 by pressing sample acquisition device 120 towards wound 40 such that capillary array 16 presses into wound 40. As the user presses capillary array 16 into wound 40, first portion 124 of stem 122 moves toward head 14, thereby compressing spring 128 against wall 130. FIG. 11B illustrates spring 128 in a compressed state. As first stem portion 124 moves into second stem portion 126, the total length L of stem 122 changes, thereby providing feedback to the user that changes as the pressure applied to wound 40 changes. In this way, spring 128 and stem 122 provide a tactile indication to the user to indicate the relative amount of pressure applied toward wound 40.

In some embodiments, sample acquisition device 120 may include visible markers 132 that provide visual indicia for indicating the relative amount of movement between first portion 124 and second portion 126 of stem 122. When spring 128 is in a unstressed (noncompressed) state (as shown in FIG. 11A), a baseline number of markers 132 are visible to the user. In the embodiment shown in FIG. 11A, five markers 132 are visible to the user when spring 128 is in an uncompressed state. In other embodiments, sample acquisition device 120 may include any suitable number of markers.

As the user presses down on stem 122, spring 128 compresses and first portion 124 of stem 122 moves into second portion 126. As first stem portion 124 moves into second stem portion 126, some markers 132, which are in a fixed position on first stem portion 124, also move into second portion 126. Thus, as pressure is applied to wound 40 and first stem portion 124 moves into second stem portion 126, the number of markers 132 that remain visible outside of second portion 126 of stem 122 decreases, thereby providing a visual indication of movement between first portion 124 and second portion 126 of stem 122. The number of markers 132 that remain outside of second stem portion 126 varies with the pressure the user applies to wound 40. In some embodiments, first and second portions 124, 126 of stem 122 are substantially opaque, such that markers 132 that are disposed within second portion 126 of stem 122, as indicated by markers 132' in FIG. 11B, are not visible to a user. In the embodiment shown in FIG. 11B, when spring 128 is in a completely compressed state (i.e., cannot compress any more), two markers 132 are visible.

Markers 132 may help guide the use of sample acquisition device 120. For example, a manufacturer or distributor of sample acquisition device 120 may provide guidelines relating to the desirable pressure to be applied to various types of sample sources in order to acquire a sufficient amount of sample. The pressure may be stated in terms of the number of markers 132 that should remain exposed while capillary array 16 is placed in contact with sample source. In addition, markers 132 may help a user use sample acquisition device 120 in a substantially consistent way. For example, after multiple trials, the user may determine that damage or agitation to wound 40 is minimized and a sufficient amount of sample is acquired when capillary array 16 is held in contact with wound 40 with a pressure that results in three markers 132 remaining exposed outside of second stem portion 126.

In one embodiment, visible markers 132 may be representative of units of measurement (e.g., millimeters or centimeters), and, in some embodiments, labeled with numbers representing units of measurement. Markers 132 may be printed markings on first portion 124 of stem 122, indentations defined by first portion 124, or another type of marker that is visible or otherwise detectable.

Figure 12A:
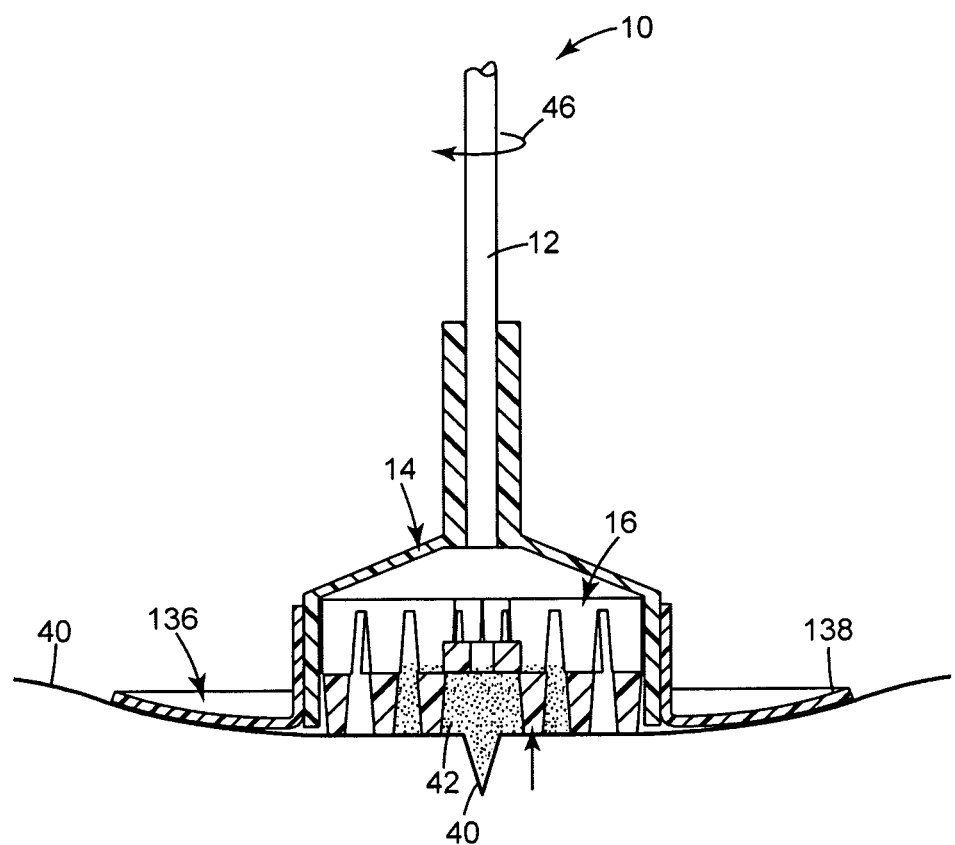
FIGS. 12A and 12B illustrate an embodiment of a capillary array tip.
Figure 12B:
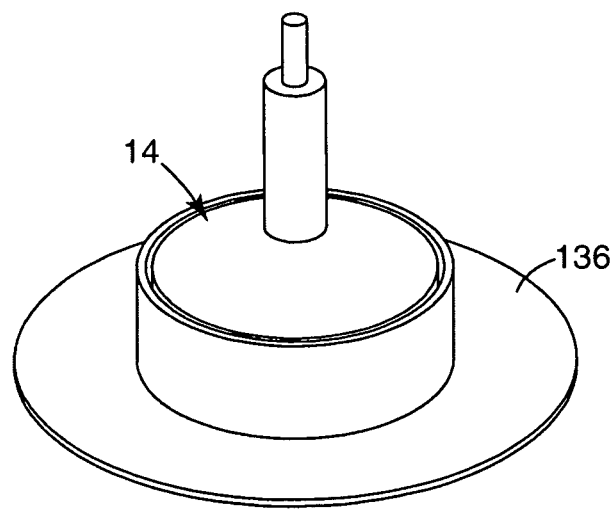

The technique employed to acquire a sample with a sample acquisition device including a capillary array 16 may vary depending upon the type of sample acquisition source. With some sample acquisition sources, application of a particular pressure to the source may be desirable in order to express more exudates from the sample source. As another example, with some sample acquisition sources, moving sample acquisition surface 22 of capillary array 16 in a particular pattern relative to the source may be desirable. Accordingly, in some embodiments, a tip with features that personalize a sample acquisition device to a particular sample source may be attached to the sample acquisition device. The tip may, for example, accommodate a particular sample acquisition technique. FIGS. 12A and 12B are schematic illustrations of embodiments of tips. While sample acquisition device 10 (FIG. 1) is primarily referred to throughout the description of FIGS. 12A-14, in other embodiments, a tip may be applied to other types of sample acquisition devices, such as sample acquisition device 60 (FIGS. 6A-6B), sample acquisition device 110 (FIGS. 10A-10B) or sample acquisition device 120 (FIGS. 11A-11B).

FIGS. 12A and 12B illustrate rounded tip 136 coupled to head 14 of sample acquisition device 10. Rounded tip 136 helps distribute pressure applied to wound 40 over a larger area in order to more efficiently express sample 42 from wound 40 and capture sample 42 in capillary array 16. Some wounds 40, such as an abrasion or laceration, express more exudate as more pressure is applied to wound 40. Accordingly, tip 136 centers capillary array 16 relative to the region in which wound 40 is depressed the most, as shown in FIG. 12A, thereby helping to maximize the amount of sample 42 that is captured within capillary array 16. In addition, tip 138 positions capillary array 16 away from regions of wound 40, e.g., region 138, in which less exudate is expressed when wound 40 is depressed.

Tip 136 may couple to head 14 of sample acquisition device 10 via any suitable technique. In some embodiments, tip 136 is removably attached to head 14 via a friction fit (shown in FIG. 12A), an adhesive, interlocking parts or the like. In other embodiments, tip 136 is permanently attached to head 14 (i.e., is not easily removable from head 14 without substantially damaging head 14) via any suitable technique, such as ultrasonic welding, an adhesive or the like. Alternatively, head 14 and tip 136 may be an integral element. Head 14 may be configured to couple to various types of tips. A user may select a tip that best accommodates the particular type of sample source or sample acquisition technique employed by the user.

Figure 13:
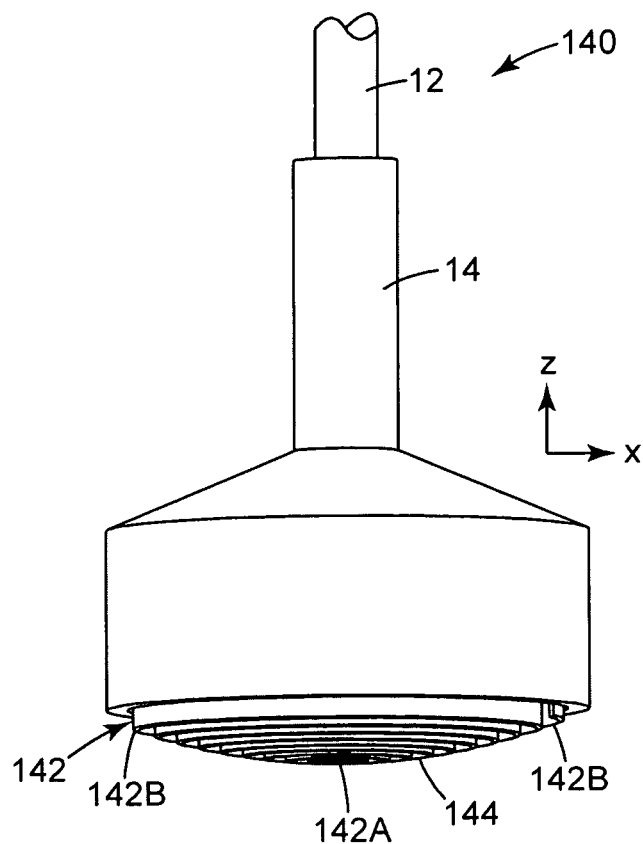
FIG. 13 is a perspective view of an embodiment of a sample acquisition device that includes a rounded capillary array.

FIG. 13 is a perspective view of another embodiment of sample acquisition device 140, which is substantially similar to sample acquisition device 10 (FIG. 1), but includes capillary array 142 defining a curvilinear sample acquisition surface 144. Capillary array 142 provides a function substantially to the rounded tip 136 of FIGS. 12A and 12B. In particular, the shape of rounded capillary array 142 may help center the pressure applied to wound 40 relative to capillary array 142 while avoiding possible damage to the wound surface due to a sharp square edge shown in FIG. 1. Sample acquisition surface 144 is curvilinear, such that a center 142A of capillary array 142 extends further from head 14 (along the z-axis, where orthogonal x-z axes are shown in FIG. 13) than edges 142B. While sample acquisition surface 144 of capillary array 142 is not planar, major sample acquisition surface 144 remains oriented substantially perpendicular to a major axis 24 of stem 12.

Although capillary array 142 is shown to have a circular cross-sectional shape (i.e., along the x-y plane) in FIG. 13, in other embodiments, capillary array 142 may have another cross-sectional shape, such as a square, rectangular, elliptical, oval or triangular cross-section.

Figure 14:
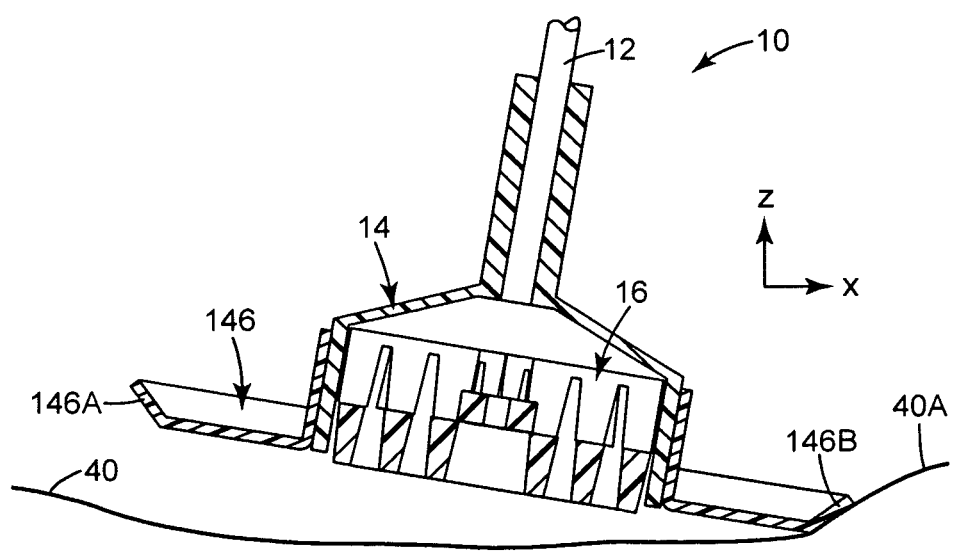
FIG. 14 is a schematic cross-sectional view of another embodiment of a capillary array tip.

FIG. 14 is a schematic cross-sectional view of sample acquisition device 10, which includes another embodiment of tip 146 coupled to head 14. Rather than defining a curvilinear surface for contacting wound 40, as with tip 136, tip 146 defines flexible pads 146A and 146B for pressing around the edge of wound 40. In FIG. 14, flexible pad 146B is pressed against one edge 40A of wound 40. Tip 146 may be useful for acquiring a sample from a wound 40 that expresses more exudate from a center portion when pressure is applied to the edges 40A. Rather than moving a position of sample acquisition device 10 relative to wound 40 in order to press edges 40A of wound 40, a user may rock device 10 relative to wound 40 in order to press edges 40A of wound 40 with the aid of tip 146. Rocking head 14 of device 10 relative to wound 40 enables capillary array 16 to remain positioned above a center portion of wound 40 and capture the exudate as it exits wound 40. In contrast, exudate may be displaced if a user moves capillary array 16 generally along the x-y plane (orthogonal x-z axes are shown in FIG. 14 and the y-axis extends substantially perpendicular to the plane of the image in FIG. 14) relative to wound 40 in order to apply pressure to the edges 40A of wound 40.

Thus, tip 146 may provide a more efficient technique for expressing sample from wound 40 by enabling the user to substantially maintain the x-axis and y-axis position of sample acquisition device 10 while expressing exudate from wound 40. As with tip 136 of FIGS. 12A and 12B, tip 146 may removably or permanently couple to head 14 of sample acquisition device 10 via any suitable technique, such as the techniques described with respect to tip 136.

Figure 15A:
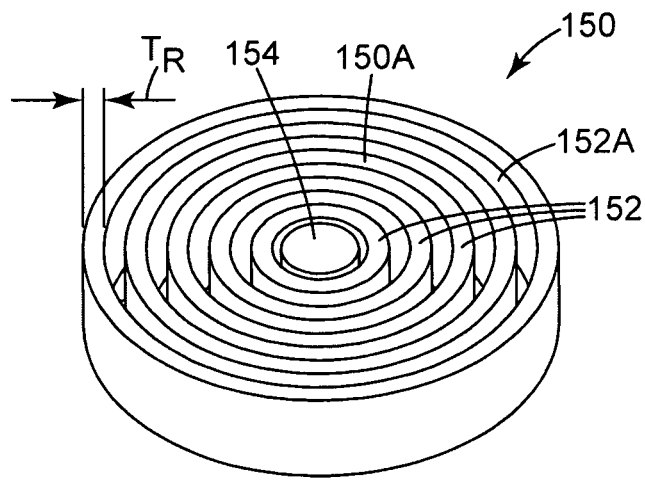
FIGS. 15A-15E illustrate embodiments of different types of capillary arrays.

FIGS. 15A-15E are schematic perspective views of various embodiments of capillary arrays that may be used to acquire and retain a sample by capillary action. In FIG. 15A, capillary array 150 is defined by a plurality of concentric rings 152. Capillary array 150 is similar to capillary array 16 of FIG. 1. The distance between rings 152 may affect the capillary pressure exhibited by capillary array 150, as well as the ability for capillary array 150 to retain a sample. A center of capillary array 150 is occupied by nub 154. In embodiments in which rinse fluid is introduced into a lumen of a stem, nub 154 may help prevent the rinse fluid from flushing directly out the center of array 150 and miss the rest of the array 16. In one embodiment, rings 152 are separated from adjacent circles by a distance of about 0.5 mm. In some embodiments, at least two of the rings 152 may have same thicknesses $T_R$, which is measured along a sample acquisition surface of capillary array 150. In some embodiments, rings 152 may be comprised of a relatively flexible polymer, such as a silicone rubber or a suitable thermoelastomer in order to reduce damage to the wound surface.

A diameter of outermost ring 152 may be in a range of about 0.5 mm to about 1.5 mm, such as about 1.0 mm. In one embodiment, a ratio of the area of sample acquisition surface 150A of capillary array 150 to the maximum sample volume retained by capillary array 150 is about 0.151 mL/mm$^2$ to about 0.201 mL/mm$^2$, such as about 0.176 mL/mm$^2$. Sample acquisition surface 150A is a continuous surface defined by capillary array 150 substantially in the x-y plane. In some embodiments, however, sample acquisition surface 150A may not be substantially planar (e.g., may be curvilinear). Although five rings 152 are shown in FIG. 15A, in other embodiments, capillary array 150 may include any suitable number of circles separated from each other by any suitable distance.

Figure 15B:
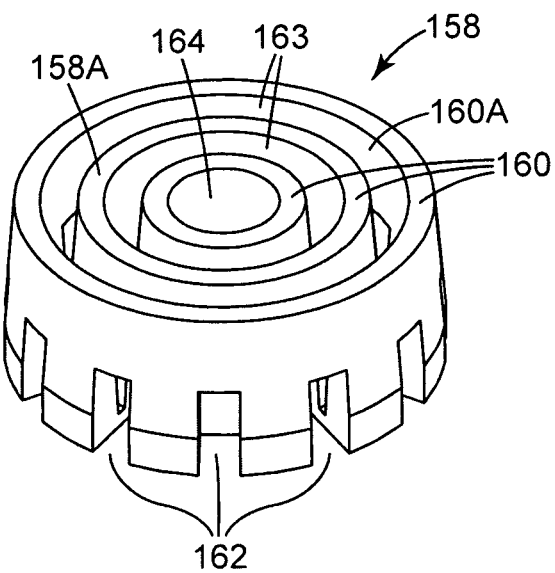

FIG. 15B illustrates capillary array 158, which is also defined by a plurality of concentric circles 160. However, unlike rings 152 of capillary array 150 (FIG. 15A), circles 160 define a plurality of distribution channels 162 that fluidically connect each capillary channel 163 defined between circles 160. Thus, capillary array 150 may define a common sample acquisition region. Distribution channels 162 joining capillary channels 163 help distribute an acquired sample throughout capillary array 158, which may increase the speed at which capillary array 158 acquires a sample compared to capillary array 150 of FIG. 15B. For example, it is believed that passageways 162 may help vent capillary channels 163, which may aid the sample intake process.

A center of capillary array 158 defines a well 164 for receiving and retaining sample 42 from wound 40 or another sample source. In one embodiment, a ratio of the area of sample acquisition surface 158A of capillary array 158 to the maximum sample volume retained by capillary array 158 is about 0.163 mL/mm$^2$ to about 0.213 mL/mm$^2$, such as about 0.188 mL/mm$^2$.

Figure 15C:
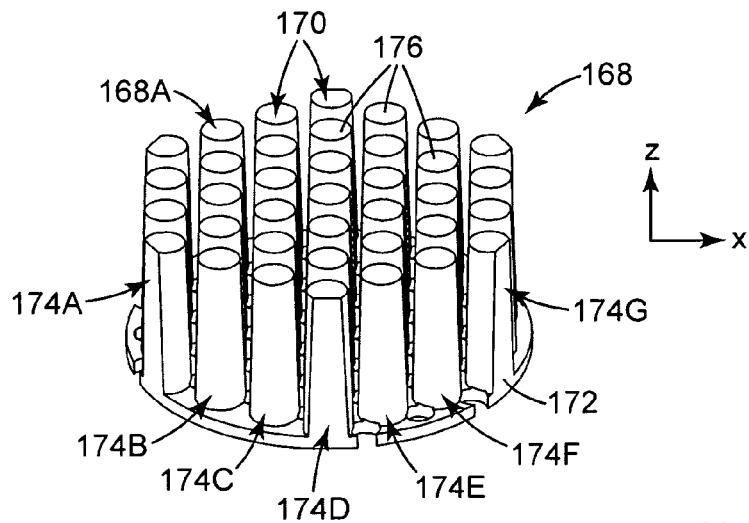

FIG. 15C illustrates another embodiment of a capillary array 168, which includes an array of protrusions 170 extending from a common platform 172. Protrusions 170 are substantially similar in diameter (measured substantially along the x-y plane, where orthogonal x-y-z axes are shown in FIG. 15C), but have different heights (measured substantially along the z-axis). In the embodiment shown in FIG. 15C, protrusions 170 are arranged seven columns 174A-G, where each column of protrusions has a different height than an adjacent column. Columns 174C and 174E have substantially equal heights, columns 174B and 174F have substantially equal heights, and columns 174A and 174G have substantially equal heights. The heights of columns 174A-G are arranged such that center column 174D has the greatest height, i.e., extends the furthest from a substantially planar platform 172, and the heights of the other protrusions 170 gradually decrease, such that protrusions 170 of rows 174A and 174G are the shortest, i.e., extend the least from a substantially planar platform 172. Thus, protrusions 170 define a sample acquisition surface 176 that is curvilinear in at least one cross-section (i.e., along the x-z plane). In some cases, rows of protrusions 170, which extend in a direction substantially perpendicular to columns 174A-G, also have varying heights such that a center protrusion has the greatest height and the height of the remaining protrusions gradually decrease radially outward to define a sample acquisition surface 176 that is rounded in two dimensions (i.e., along the x-axis direction as well as the y-axis direction).

Although protrusions 170 including substantially circular cross-sections are shown in FIG. 15C, in other embodiments, capillary array 168 may include protrusions having other cross-sectional shapes, such as square, rectangular, elliptical, triangular, and so forth. In addition, in other embodiments, platform 172 may be another shape. In some embodiments, platform 172 may not be substantially planar, but may be curvilinear such that protrusion 170 having substantially equal heights define a substantially rounded sample acquisition surface 176. In one embodiment, a ratio of the area of sample acquisition surface 168A of capillary array 168 to the maximum sample volume retained by capillary array 168 is about 0.216 mL/mm$^2$ to about 0.266 mL/mm$^2$, such as about 0.241 mL/mm$^2$.

Figure 15D:
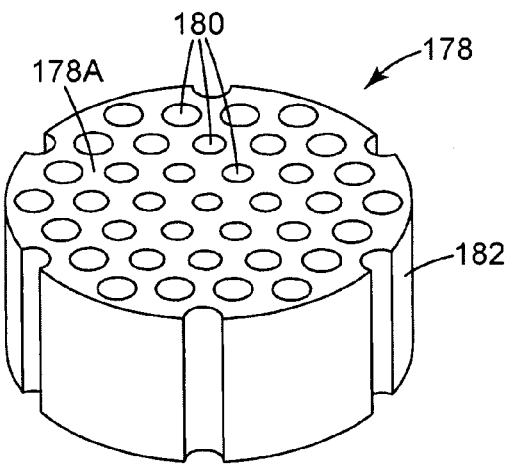

FIG. 15D illustrates another embodiment of a capillary array 178, which includes an array of apertures 180 arranged into a plurality of columns. Apertures 180 are defined by a common member 182. In the embodiment shown in FIG. 15D, apertures 180 vary in size. In other embodiments, apertures 180 may have substantially uniform sizes, but need not each be a symmetrical shape. The size of each aperture 180 as well as the arrangement of apertures relative to each other may be selected to hold a particular volume of a sample, as well as to achieve a particular capillary action to draw the sample into each aperture 180 within a particular time span. In one embodiment, a ratio of the area of sample acquisition surface 178A of capillary array 178 to the maximum sample volume retained by capillary array 178 is about 0.140 mL/mm$^2$ to about 0.190 mL/mm$^2$, such as about 0.165 mL/mm$^2$.

Figure 15E:
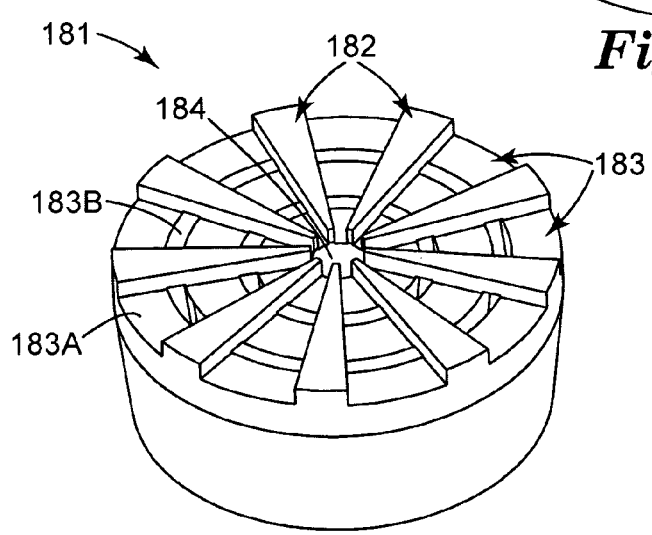

FIG. 15E illustrates another embodiment of a capillary array 181, which includes a plurality of structures 182 defining sample acquisition and distribution regions 183 that may be in fluidic communication with each other via an open center portion 184. Capillary array 181 acquires a sample by capillary force. FIG. 15E illustrates a surface of capillary array 181 that is substantially opposite the sample acquisition surface. The sample acquisition surface (not shown) may include a plurality of concentric circles that define capillary channels, as shown with sample acquisition surface 22 in FIG. 1. Structures 182 extend radially outward from center 184 to define regions 183. Sample acquisition regions 183 are defined by portions 183A that fluidically couple channels 183B. In the embodiment shown in FIG. 15E, channels 183B are concentric. However, in other embodiments, channels 183B may have any suitable configuration.

Figure 16A:
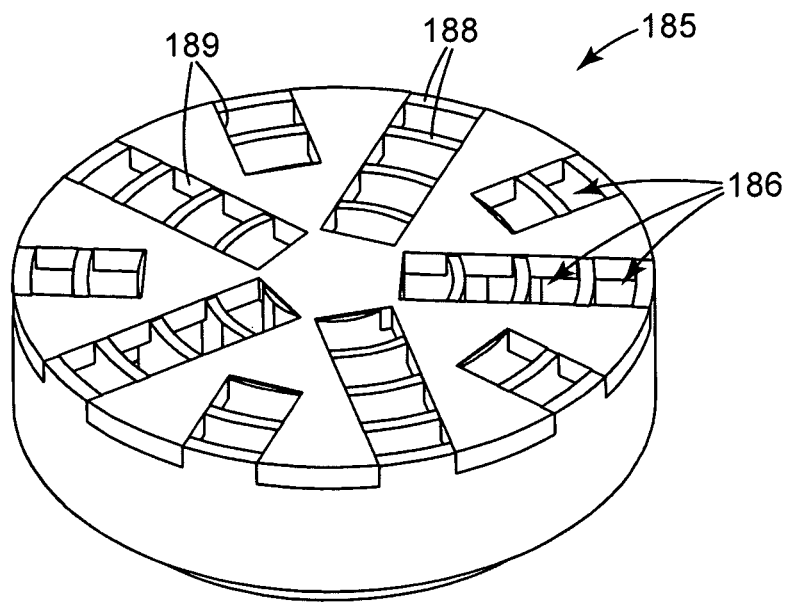
FIGS. 16A and 16B illustrate perspective views of opposite sides of another embodiment of a capillary array.
Figure 16B:
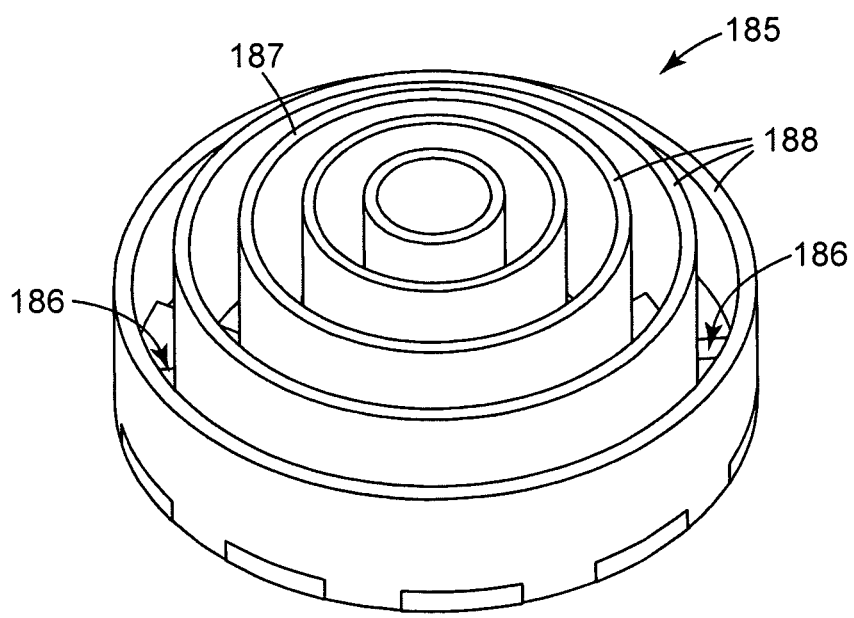

FIGS. 16A and 16B illustrate perspective views of opposite sides of another embodiment of capillary array 185, which defines a plurality of sample acquisition regions 186 that acquire a sample from a sample source with the aid of capillary action. FIG. 16B illustrates a nonplanar sample acquisition surface 187 of capillary array 185. Capillary array 185 defines a plurality of concentric structures 188, and sample acquisition regions 186 are channels defined between concentric circles 188. Thus, sample acquisition regions 186 are separated by structures 188, but are fluidically coupled via openings 189 on a surface of capillary array 185 substantially opposite sample acquisition surface 187. In other embodiments, however, sample acquisition regions 186 may be fluidically isolated from an adjacent sample acquisition region 186.

Figure 17A:
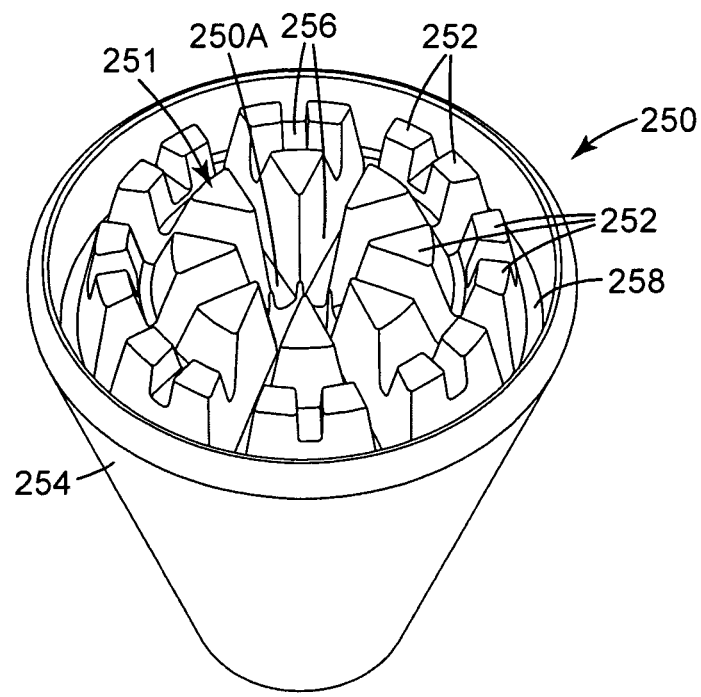
FIGS. 17A and 17B illustrate a perspective view and a schematic cross-sectional view, respectively, of another embodiment of a capillary array.
Figure 17B:
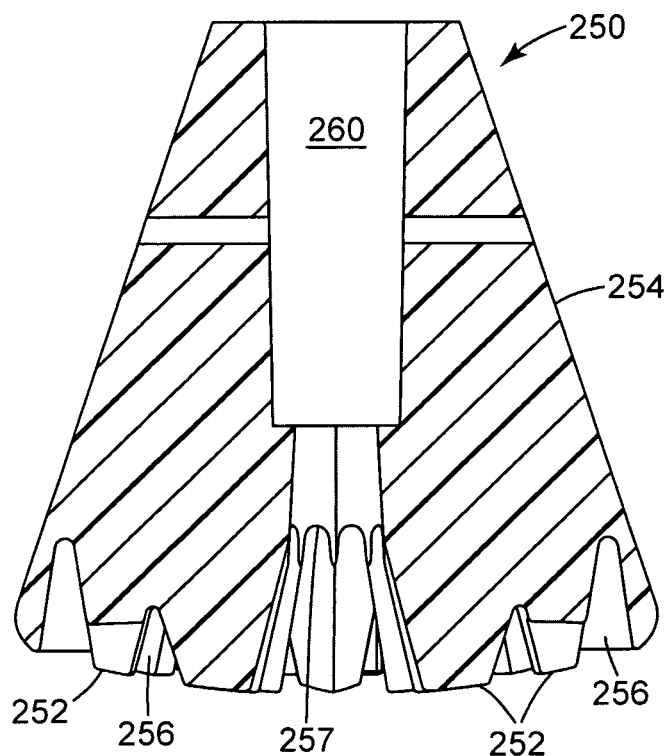

FIGS. 17A and 17B illustrate a perspective view and schematic cross-sectional view of another embodiment of capillary array 250, which includes a plurality of structures 252 defined by a common member 254. FIG. 17A illustrates a sample acquisition surface 251 of capillary array 250. In the embodiment shown in FIGS. 17A and 17B, structures 252 are substantially integral such that capillary array 250 is a unitary structure. In other embodiments, at least two of the structures 252 may be coupled together with any suitable technique, e.g., an adhesive, interconnecting parts or welding. Structures 252 define a plurality of sample acquisition regions 256 that acquire and retain a sample by capillary action. In this manner, sample acquisition regions 256 define an array of capillaries.

Sample acquisition regions 256 radially extend between a center region 250A of capillary array 250 and an outer peripheral channel 258. Channel 258 may also define a sample acquisition region that acquires and retains a sample by capillary action. In addition, channel 258 may help vent sample acquisition regions 256 when sample acquisition surface 251 is at least partially engaged with a sample source, such as wound 40. In the embodiment shown in FIGS. 17A and 17B, sample acquisition regions 256 are in fluidic communication with each other. Rounded surfaces 257 of sample acquisition regions 256 may help minimize the binding of sample particles to capillary array 250 within sample acquisition regions 256, which may help improve the elution rate of sample particles from capillary array 250.

Just as with the previous capillary arrays, structures 252 of capillary array 250 may be configured such that sample acquisition regions 256 retain a maximum sample volume in order to help meter the quantity of sample that may be acquired with capillary array 250. In some embodiments, common member 254 may be directly coupled to stem 12 (FIG. 1) to define a sample acquisition device. For example, common member 254 may define an opening 260 configured to engage with stem 12 by interference fit.

Figure 18:
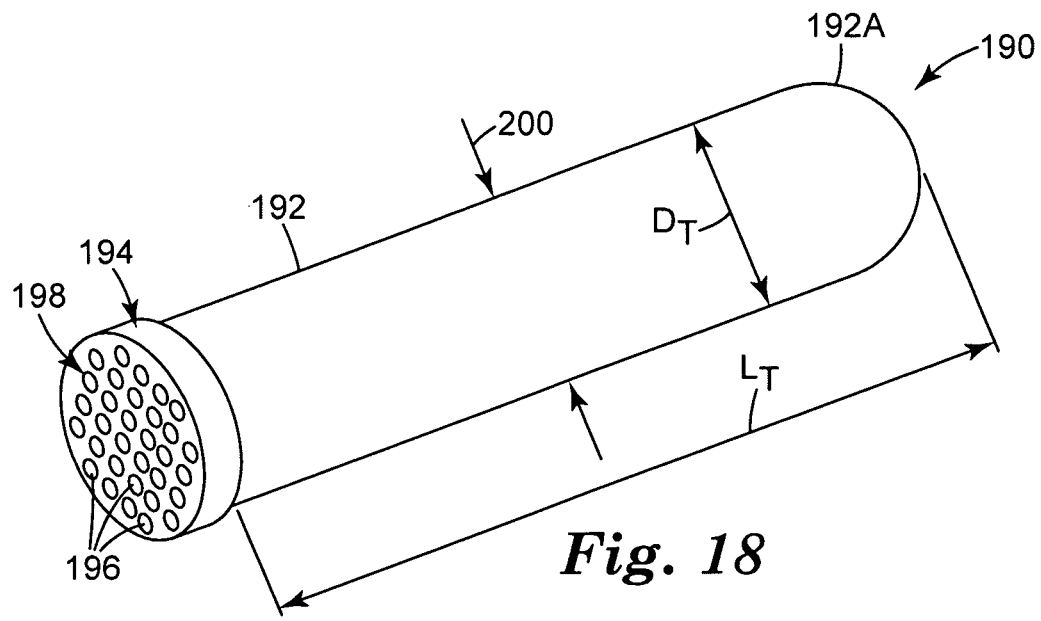
FIG. 18 is a perspective view of another embodiment of a sample acquisition device, which includes a vacuum source.

In each of the embodiments of sample acquisition devices described above, the capillary arrays acquired a sample from a sample source via capillary action resulting from the relative surface energies of the material comprising the capillary array and the sample, without the aid of additional acquisition forces. FIG. 18 is a perspective view of another embodiment of a sample acquisition device 190 that acquires a sample from a sample source with the aid of capillary action and a suction source. Sample acquisition device includes tube 192, which is coupled to a head 194 that defines a plurality of capillary apertures 196. Capillary apertures 196 are arranged into a plurality of rows and columns that define a capillary array 198. Capillary apertures 196 each define a sample acquisition region. In some embodiments, some of capillary apertures 196 are not in fluidic communication with each other, while in other embodiments, at least some of capillary apertures 196 may be in fluidic communication.

Tube 192 defines a substantially hollow inner lumen, which is closed off at a proximal end 192A, where the inner lumen is in fluidic communication with capillary array 198. Thus, fluid, such as a liquid rinse liquid or a gas (e.g., air), flowing through tube 192 may also flow through capillary apertures 196. Tube 192 may have a diameter $D_T$ of about 0.5 cm to about 1.5 cm, such as about 0.8 cm. A length $L_T$ of tube 192 may be in a range of about 50 mm to about 200 mm, such as about 125 mm.

When capillary array 198 is placed into contact with wound 40, sample 42 may enter at least some of apertures 196 via capillary action. In order to aid the adsorption of sample 42 into capillary array 198, tube 192 may provide a suction force to draw sample 42 into apertures 196, i.e., to aspirate sample 42 from wound 40. In one embodiment, prior to or after capillary array 198 is placed into contact with wound 40, a user may squeeze tube 192, such as indicated by arrows 200, thereby effectively decreasing the volume within the inner lumen defined by tube 192, and decreasing the amount of air contained within the inner lumen defined by tube 192. After the user releases tube 192, the volume within tube 192 expands, reducing the pressure within tube 192 and creating a partial vacuum. In order to equilibrate pressures within tube 192 and outside of tube 192, air from outside of tube 192, i.e., outside of apertures 196 is drawn into tube 192, along with sample 42, which moves into apertures 196. In this way, hollow tube 192 is may be a suction source. In other embodiments, sample acquisition device 190 may include another suction source, such as a suction syringe, to aid the acquisition of sample 42 in apertures 196.

Tube 192 may be comprised of any suitable compliant material, such as a compliant polymer, e.g., polyethylene, polypropylene or polycarbonate. The thickness of the material forming tube 192 may be modified to achieve the desired suction force. Although not shown in FIG. 18, in some embodiment, a filter or a flow distributor may be disposed between the inner lumen of tube 192 and capillary array 198 in order to help distribute the flow of fluid, e.g., air, through apertures 196.

Figure 19A:
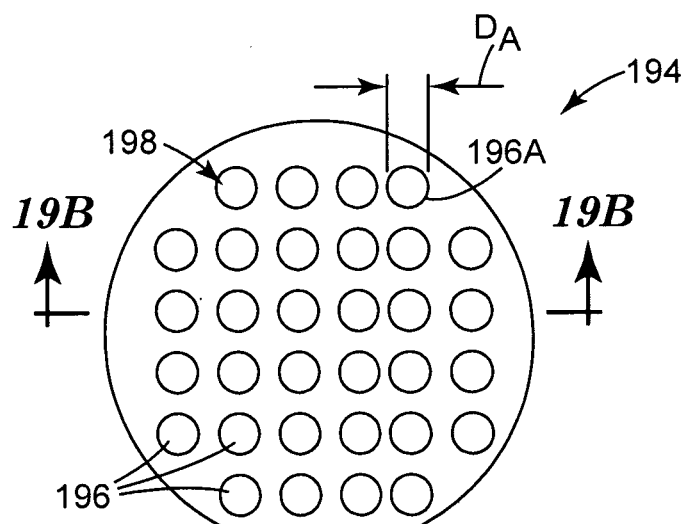
FIGS. 19A and 19B are a plan view and a schematic cross-sectional view, respectively, of the capillary array of the sample acquisition device of FIG. 18.
Figure 19B:
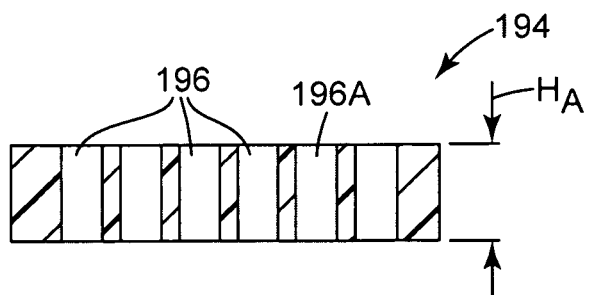

FIG. 19A illustrate a plan view of head 194, illustrating capillary array 198 and FIG. 19B illustrates a cross-sectional view of capillary array 198 taken along line 19B-19B in FIG. 19A. As FIG. 19A illustrates, apertures 196 are arranged in a plurality of rows and columns. In the embodiment shown in FIG. 19A, apertures 196 are symmetrically arranged in size columns and size rows. In other embodiments, however, apertures 196 may be otherwise arranged, i.e., arranged in irregular rows and columns or arranged in a formation other than linear rows and/or columns. As shown in FIG. 19B, apertures 196 are defined by a common structure, i.e., head 194.

Aperture 196A, which is representative of each of apertures 196, has a diameter $D_A$, and a height $H_A$. Diameter $D_A$, height $H_A$, as well as the number of apertures 196 in array 198, may be selected based on the maximum volume of sample 42 to be acquired and retained by sample acquisition device 190. Aperture 196A may hold a maximum sample volume (i.e., $pi*(\frac{1}{2}D_A)^2*H_A$), and, accordingly, a total volume of array 198 may be calculated by multiplying the volume of aperture 196A by the total number of apertures 196. In the embodiment shown in FIG. 19A, capillary array 198 is configured to hold a maximum volume of about 80 μL to about 390 μL such as about 100 μL.

The size of aperture 196A may also be selected based on the material of head 194 because, in some cases, the size of aperture 196A may affect the capillary action exhibited by apertures 196A relative to a viscosity of sample 42, as well as the ability of aperture 196A to retain sample until eluted by a user. For example, once a particular ratio in diameter $D_A$ to height $H_A$ of aperture 196A is reached, any increase in diameter $D_A$ relative to height $H_A$ may diminish the capillary force exhibited by aperture 196A. The capillary force may also depend upon the surface energy of the material defining aperture 196A and the surface energy of the sample.

FIGS. 20A and 20B illustrate an embodiment of a technique that may be employed to acquire a sample from wound 40 with sample acquisition device 190 and release sample 42 from sample acquisition device 190. A user may place capillary array 198, which is defined by head 194, in contact with wound 40 in order to draw sample 42 into capillary array 198 by capillary force. A user may squeeze tube 192, e.g., with his fingers, as indicated by arrows 200, in order to aspirate sample 42 from wound 40 and draw sample 42 into capillary array 198. Drawing sample 42 into capillary array 198 with the aid of suction force enables capillary array 198 to be formed of a material having a lower surface energy than a capillary array that is not used in conjunction with a suction source. The lower surface energy material may exhibit better sample release characteristics.

After acquiring sample 42 from wound 40, the user may withdraw sample acquisition device 190 from the sample source and cover head 194 with a cap for storage (not shown) or otherwise store sample acquisition device 190. Prior to sample preparation and analysis, the user may elute sample 42 from capillary array 198 by fluidically coupling bulb 202 to head 194. Bulb 202 stores rinse fluid 204. As with bulb 62 (FIGS. 6A and 6B), in some embodiments, bulb 202 may store a volume of rinse fluid 204 that is proportional to the maximum volume of sample capillary array 198 is engineered to retain.

In some embodiments, head 194 may mechanically couple to bulb 202 by friction fit, interlocking parts, adhesive or by any other suitable technique. Bulb 202 is removably coupled to head 194 such that device 190 includes a first state in which capillary array 198 is exposed and may be placed in contact with a sample source, and a second state in which bulb 202 is coupled to head 194. Bulb 202 defines an opening 206 that fluidically couples to capillary array 198. In the embodiment shown in FIG. 20B, opening 206 and head 194 are sized to mate together and define a substantially fluid-tight seal, such that fluid 204 flows through capillary array 198, rather than around an exterior surface of head 194. After bulb 202 is coupled to head 194, the user may open a valve that retains fluid 204 within bulb in order to release fluid 204 from bulb 202. For example, bulb 202 may include a snap valve similar to snap valve 68 of bulb 60 (FIGS. 6A-6B) or a thin membrane that may be ruptured with or without the aid of additional tools. In order to encourage the flow of rinse fluid 204 from bulb 202 and the pressure with which fluid 204 flows through capillary array 198, the user may squeeze bulb 202.

As shown in FIG. 20B, as rinse fluid 204 flows from bulb 202 through capillary array 198, sample 42 is eluted from capillary array 198. Sample 42 may accumulate at distal end 192A of tube 192, along with rinse fluid 204 that is released from bulb 202. The user may then perform any desired sample preparation and analysis techniques using the mixture comprising sample 42 and rinse fluid 204. Although not shown in FIG. 19B, in some embodiments, a filter or a flow distributor may be disposed between bulb 202 and capillary array 198 in order to help distribute the flow of the rinse fluid 204 through apertures 196 and more efficiently wash sample 42 from head 194.

FIGS. 22A-22C illustrate the results of an experiment comparing the quantity of aerobic bacteria (measured in colony forming units (CFU)/mL) acquired from a sample source for four types of sample acquisition devices. The devices included a conventional swab including a rayon bulb tip (available from Copan Diagnostics Inc. of Murrieta, Calif.), a swab provided under the trade name ESwab by Copan Diagnostics, Inc., sample acquisition device 10 including capillary array 16 (FIGS. 1-4), and sample acquisition device 190 including a suction source 192 and capillary array 198 (FIG. 19A-19B). The sample source was the interior cheek surface of a human patient, which is also referred to as a buccal cavity.

Natural bacterial flora reside within the interior cheek surface, which is typically also a naturally moist surface.

FIGS. 21A-21C illustrate the results of an experiment in which the three different sample acquisition devices were swabbed at different points on the cheek using the Levine technique, which is discussed above. In particular, the rayon bulb of the convention swab, capillary array 16, and capillary array 198 were placed in contact with the tissue in the buccal cavity such that the stem 12 of the respective sample acquisition device was held substantially perpendicular to the tissue's surface. For each of the devices, pressure was applied while rotating the rayon bulb, capillary array 16, and capillary array 198 within a 1 cm$^2$ area of the tissue surface for about five seconds. For sample acquisition device 190 (FIG. 18) including capillary array 198, tube 192 was used to apply suction as capillary array 198 was held in contact with the tissue surface. The buccal cavity was sampled "wet" or "dry." "Wet" sampling was performed for the buccal cavity without any removal or addition of moisture, while "dry" sampling was performed on a buccal cavity that had been dried using cotton gauze.

After sample collection, the conventional rayon swab, capillary array 16 and capillary array 198 were placed into a sterile tube containing an elution buffer comprising about 1.0 mL of a phosphate buffer saline (PBS) solution. The PBS solution was prepared by diluting ten-fold (10×) PBS liquid concentrate (commercially available from EMD Biosciences, Inc. of San Diego, Calif.). The resulting PBS buffer solution included the following salt composition: 10 milliMols (mM) of sodium phosphate, 137 mM of sodium chloride, and 2.7 mM of potassium chloride. The resulting PBS buffer solution had a pH of about 7.5 at a temperature of about 25° Celsius. A batch of PBS was also prepared with a PLURONIC L64 solution (PBS-L64 buffer solution). In particular, 0.2% (weight by volume (w/v)) of the PLURONIC L64 surfactant (available from BASF Corporation of Florham Park, N.J.) was added to the PBS buffer solution. The resulting PBS-L64 buffer solution had a pH of about 7.5 at about 25° C. After sample collection, the ESwab was placed in the tube accompanying the E Swab system, which included an elution buffer.

In FIGS. 22A and 22B, the collected samples were then eluted from the respective sample acquisition devices by machine vortexing the device in the respective elution buffer for about 30 seconds. Efforts were made to ring, tap, or squeeze excess elution buffer from the devices. The devices were then removed from the elution buffer. The number of viable bacteria in each of the eluted samples was determined by plating serial dilutions of each sample on a ready-made culture medium system that includes Standard Methods nutrients, a cold-water-soluble gelling agent, and an indicator that facilitates colony enumeration, where the system is available under the name Petrifilm Aerobic Count Plates (from 3M Company of St. Paul, Minn.).

FIG. 22A illustrates the aerobic bacterial counts when the samples were acquired from a "wet" buccal cavity with the conventional rayon swab, device 10 including capillary array 16, and device 190 including capillary array 198. The results shown in FIG. 22A compare the viable aerobic bacterial count recovered from the rayon swab, device 10 including capillary array 16, and device 190 including capillary array 198 after sample collection at three different tissue sites and elution for three replicates. The results shown in FIG. 22A suggest that the device 10 including capillary array 16 that acquires a sample with the aid of capillary force and device 190 including capillary array 198 that acquires a sample with the aid of capillary force and a suction source (i.e., tube 192) have a sample acquisition performance that is comparable to the conventional rayon swab. In particular, the average aerobic bacterial count for the rayon swab was about 250,000 CFU/mL, while the average aerobic bacterial count for device 10 was about 200,000 CFU/mL and the average aerobic bacterial count for device 190 was about 230,000 CFU/mL.

FIG. 22B illustrates the aerobic bacterial counts when the samples were acquired from a "dry" buccal cavity with the conventional rayon swab, the ESwab, device 10 including capillary array 16, and device 190 including capillary array 198. The results shown in FIG. 22B compare the viable aerobic bacterial count recovered from each device after sample collection and elution. The results shown in FIG. 22B suggest that device 10 including capillary array 16 that acquires a sample with the aid of capillary force and device 190 including capillary array 198 that acquires a sample with the aid of capillary force and a suction source (i.e., tube 192) have a sample acquisition performance that is comparable to the conventional rayon swab and ESwab.

In particular, the average aerobic bacterial count for the sample taken from a dry cheek surface was about 350,000 CFU/mL for the conventional rayon swab and about 610,000 CFU/mL for the ESwab, while the average aerobic bacterial count for device 10 was about 260,000 CFU/mL and the average aerobic bacterial count for device 190 was about 150,000 CFU/mL.

FIG. 22C illustrates the aerobic bacterial counts when the samples were acquired from a "wet" buccal cavity with the conventional rayon swab, the ESwab, device 10 including capillary array 16, and device 190 including capillary array 198. In contrast to the results shown in FIGS. 22A and 22B, however, the collected samples were eluted from the respective devices by manually twirling the respective device in the elution buffer for about 10 seconds, i.e., without the aid of machine vortexing. For device 190, the sample was eluted by squeezing tube 192 pulling the elution buffer in and out of tube 192 and capillary array 198 for about 10 seconds.

The results shown in FIG. 22C compare the viable aerobic bacterial count recovered from the conventional rayon swab, the ESwab, device 10 including capillary array 16, and device 190 including capillary array 198 after sample collection and elution for three replicates. More particularly, the results shown in FIG. 22C compare the performance in capture and release of a sample from each type of device, where the sample is eluted from the respective device without the aid of a machine vortexer.

The results shown in FIG. 22C suggest that device 10 including capillary array 16 that acquires a sample with the aid of capillary force and device 190 including capillary array 198 that acquires a sample with the aid of capillary force and a suction source (i.e., tube 192) release a greater quantity of sample with manual techniques, i.e., without the aid of machine vortexing, compared to a conventional rayon swab and ESwab. In particular, the average aerobic bacterial count for the sample taken from a wet cheek surface was about 330,000 CFU/mL for the conventional rayon swab and about 1,580,000 CFU/mL for the ESwab, while the average aerobic bacterial count for device 10 was about 2,150,000 CFU/mL and the average aerobic bacterial count for device 190 was about 2,370,000 CFU/mL.

FIGS. 22A and 22B are a schematic perspective view and side view, respectively, of capillary array 210, which may be a part of a sample acquisition device including a stem 12, as described above. Capillary array 210 may be coupled to stem 12 that defines an inner lumen that is in fluidic communication with capillary array 210 or a suction source, such as tube 192 (FIG. 18). Alternatively, capillary array 210 may be coupled to a stem that does not define an inner lumen for receiving a fluid. Capillary array 210 includes body 212 defining a plurality of grooves 214 emanating from a common center portion 216. Body 212 defines an opening 218 configured to receive a stem, such as stem 12 or stems 74, 80, 86 or 90 shown in FIG. 1 and FIGS. 8A-8D, respectively. In some embodiments, the opening 218 may be in fluidic communication with grooves 214 such that a rinse fluid may be eluted through grooves 214 by introducing the fluid into opening 218, e.g., via a stem 74 that defines inner lumen 78 (FIG. 8A).

Body 212 defines curvilinear grooves 214 that radiate from a common center portion 216 to outer surface 222 of body 212. In the embodiment shown in FIGS. 22A and 22B, grooves 214 are interconnected and extend from common center portion 216 to a side surface 222 of body 212, which is a surface of body 212 that is adjacent to a sample acquisition surface 224 of capillary array 210. Common center portion 216 is in fluidic communication with grooves 214, such that grooves 214 and center portion 216 define a common sample acquisition region. Each of the grooves 214 curves in substantially the same direction (e.g., a clockwise direction or a counterclockwise direction) with substantially similar radius of curvature. However, each groove 214 may have varying radii of curvature along their lengths (i.e., from center portion 216 to side surface 222).

In the embodiment shown in FIGS. 22A-22C, grooves 214 have substantially similar shapes. In the embodiment shown in FIGS. 22A and 22B, groove 214A, which is similar to the other grooves 214, is defined by walls 226A, 226B that are separated by a first width $W_W$ at sample acquisition surface 224 and taper at an apex 220. Thus, walls 226A, 226B define an apex 220 that traverses substantially along from center portion 216 to an outer wall 222 of body 212. In the embodiment shown in FIGS. 22A and 22B, apex 20 is rounded. Compared to a sharp apex (e.g., an apex of a triangle), rounded apex 20 defines a surface that is more conducive to releasing sample 42 when capillary array 210 is introduced into a rinse fluid. For example, if walls 226A, 226B converge at a sharp point at apex 20, sample particles may get stuck in the small space defined at the sharp point. On the other hand, walls 226A, 226B that are joined by a curvilinear surface defines a wider space at the apex 20, thereby minimizing the possibility of sample particles binding to apex 20.

In the embodiment shown in FIGS. 22A and 22B, walls 226A and 226B of each groove 14 are substantially nonparallel to each other. In one embodiment, walls 226A and 226B are oriented at an angle of about 20° to about 160° relative to each other, such as about 45° to about 135°. In addition, in FIGS. 22A and 22B, at outer surface 222, walls 226A, 226B are angled relative to a major surface defined by sample acquisition surface 224, i.e., are not perpendicular to a major surface defined by sample acquisition surface 224. Although sample acquisition surface 224 may not be planar in all embodiments, walls 226A, 226B may still be angled relative to a plane of threshold 227, where threshold 227 is between side wall 222 and sample acquisition surface 224. As shown with groove 214B, which is substantially similar to the other grooves 214, in some embodiments, at outer surface 222, wall 226A may define an angle $A_{W1}$ of about 95° to about 160°, such as about 135°, relative to sample acquisition surface 224. In some embodiments, opposing wall 226B of groove 214B may define a complimentary angle $A_{W2}$, i.e., $A_{W2}=180-$angle $A_{W1}$. Thus, in some embodiments, angle $A_{W2}$ between wall 226B and a major surface of sample acquisition surface 224 may be about 20° to about 85°, such as about 45°. In other embodiments, angles $A_{W1}$ and $A_{W2}$ may be selected to define grooves 214 having other configurations. The angles of walls 226A, 226B relative to a major surface of sample acquisition surface 224 may or may not be consistent throughout the respective groove, i.e., between center portion 216 and side surface 222.

Capillary array 210 may be placed into contact with wound 40 to acquire sample 42. Unlike some of the other sample acquisition devices previously described, capillary array 210 may be configured such that it is desirable for a user to rotate capillary array 210 relative to wound 40 in order to acquire sample 42. When rotated in a first direction about center portion 216, as indicated by arrow 228, sample 42 is drawn into grooves 214 and center portion 216 by capillary action. Each groove 214 is shaped to define a surface that is inclined into the groove 214 when capillary array 210 is rotated in the first direction 228. Rotating capillary array 210 in a second direction about center portion 216, as indicated by arrow 230, which is substantially opposite to the first direction 228, is conducive to releasing sample 42 from grooves 214 and center portion 216. For example, capillary array 210 may be at least partially submerged in a buffer and rotated in the second direction 230 to release sample 42 from capillary array 210.

Capillary array 210 has a similar aspect ratio of the size of sample acquisition surface 224 to depth of each groove 214 as capillary array 16 (FIG. 1). In addition, capillary array 210 may be configured to hold a maximum sample volume, which may be substantially similar to capillary array 16. In some embodiments, sample acquisition surface 224 of capillary array 210 is sized to cover the wound sample area without having to move (i.e., other than rotate) capillary array 210 relative to wound 40. For example, in some embodiments, sample acquisition surface 224 has an area of about 0.1 cm² to about 1.5 cm², such as about 0.33 cm² to about 1.0 cm². In some embodiments, sample acquisition surface 228 has an area of about 1.0 cm², which supports sample acquisition via the Levine method.

Grooves 214 are interconnected to define a common capillary that receives a sample. The interconnected grooves 214 may help increase the capillary pressure with which sample 42 is acquired by increasing the outlets for venting grooves 214. For example, in embodiments in which grooves 214 are open along side wall 222, as shown in FIGS. 22A and 22B, air may vent through the portions of grooves 214 along side wall 222 as sample acquisition surface 224 is engaged with wound 40. In other embodiments, however, at least some of grooves 214 may not be interconnected. In addition, in other embodiments, grooves 214 may not be curvilinear, but, rather, may be defined by a plurality of substantially straight walls that are positioned relative to each other to define a groove that does not radiate substantially straight radially outward from center portion 216, but changes radial positions from center portion 216 to side surface 222.

FIG. 22C is a schematic perspective view of capillary array 210 coupled to stem 231 and suction source 232. In the embodiment shown in FIG. 22C, body 212 defines an inner chamber that is in fluidic communication with grooves 214. The inner chamber of body 212 and grooves 214 are in fluidic communication with an inner lumen of stem 231. Suction source 232, which may be, for example, a compressible bulb 232, is coupled to stem 231 and is in fluidic communication with the inner lumen of stem 231. A user may apply a suction force to help draw sample particles into grooves 214 by compressing and decompressing bulb 232. Bulb 232 and stem 231 provide a suction source similar to that of hollow tube 192 (FIGS. 19A and 19B).

Figure 23:
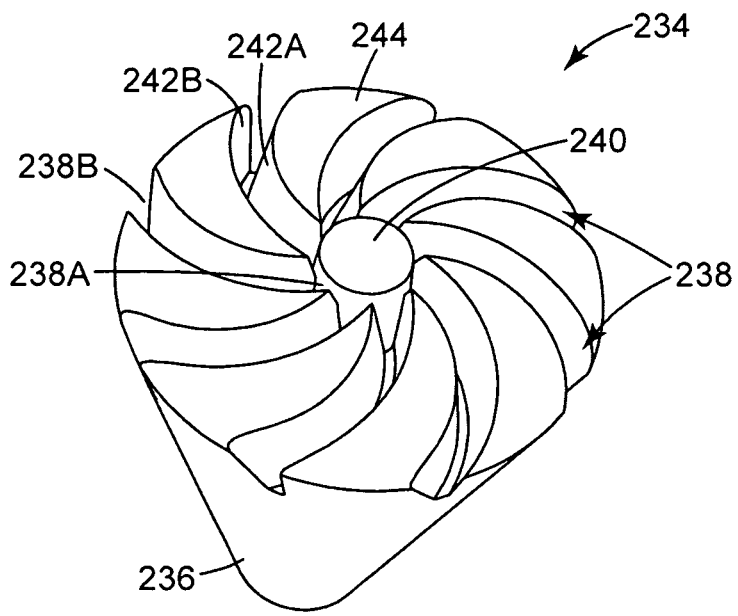
FIG. 23 is a schematic illustration of another embodiment of a capillary array that includes a body defining a plurality of interconnected grooves.
Figure 24:
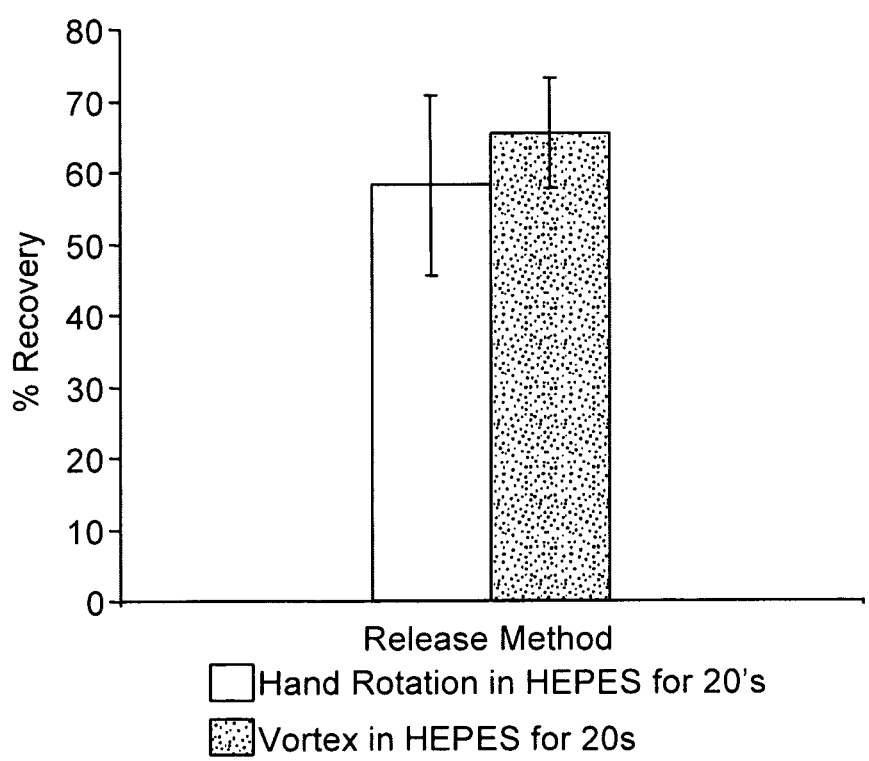
FIG. 24 is a graph illustrating the results of an experiment comparing the release of a sample from the capillary array shown in of FIG. 23 by different techniques.

FIG. 23 is a schematic perspective view of capillary array 234, which includes body 236 defining a plurality of interconnected grooves 238. Capillary array 234 is substantially similar to capillary array 210 of FIGS. 22A-22B, but includes a nub 240, instead of an open center portion 216. Just as with grooves 214 (FIGS. 22A-22B), grooves 238 are curvilinear and extend radially outward from nub 240, such that a center of base 238A of each groove 238 has a different radial position than a center of an end portion 238B of each groove 238. However, in contrast to grooves 214, each groove 238 is defined by opposing walls 242A, 242B that are substantially perpendicular to a major surface of sample acquisition surface 244 of capillary array 234 and substantially parallel to each other. In embodiments in which major surface 244 is not substantially planar, an orientation of grooves 238 may be substantially perpendicular to a planar surface on which major surface of sample acquisition surface 244 of capillary array 234 is placed. In other embodiments, however, grooves 238 may include angled walls similar to grooves 214 of FIGS. 22A-22B.

FIG. 25 is a table illustrating the results of an experiment in which sample acquisition devices ("SAD") including different types of capillary arrays, some of which were formed of different materials, were evaluated for acquisition and release characteristics. Each sample acquisition device was used to acquire a sample from a sample source, which included bacteria suspended in a buffer solution. More particularly, the sample source was a PBS including *Staphylococcus aureus* (*S. aureus* ATCC 25923, available from American Type Culture Collection of Manassas, Va.) at a concentration of approximately 4800 CFU/mL). The sample acquisition devices used in the experiment include sample acquisition device 10 including capillary array 16 (FIGS. 1-4) coupled to stem 12, a sample acquisition device including capillary array 150 (FIG. 16A) coupled to stem 12, a sample acquisition device including capillary array 158 (FIG. 16B) coupled to stem 12, a sample acquisition device including capillary array 168 (FIG. 16C) coupled to stem 12, and a sample acquisition device including capillary array 178 (FIG. 16D) coupled to stem 12.

Capillary arrays 16 formed of an epoxy based resin used in stereolitography (SLA) prototyping applications ("SLA resin"), polypropylene, polycarbonate, and silicone rubber were used in the experiment. Silicone rubber has a relatively low surface energy compared to an SLA resin, polycarbonate, and polypropylene. Capillary arrays 150, 158, 168, and 178 were each formed of an SLA resin.

Three of each capillary array 16, 150, 158, 168, 178 were dipped in approximately 5 mL of a PBS, which was prepared via the technique described above with respect to FIGS. 21A-21C, where the PBS included *Staphylococcus aureus* (*S. aureus* ATCC 25923, available from American Type Culture Collection of Manassas, Va.) at a concentration of approximately 4800 CFU/mL, for approximately 5 seconds. To prepare the bacterial suspensions for the experiment, the bacterial suspensions were prepared using overnight cultures grown in a tryptic soy broth at approximately 37° C. The cultures were centrifuged to harvest the cells and the cell pellets were resuspended in sterile PBS to a final concentration of approximately $5 \times 10^8$ CFU/mL. Prior to experimentation, the bacteria were washed in triplicate in PBS-L64 (described above with respect to FIGS. 21A-21C) and diluted to approximately $1 \times 10^4$ CFU/mL.

After dipping each capillary array 16, 150, 158, 168, 178 in the PBS including the bacteria (*Staphylococcus aureus*), each sample acquisition device was removed from the PBS and weighed on an analytical balance. The net weight of each device after the sample was acquired is shown in FIG. 25, where the weight is given in grams. The net weight reflects the approximate volume sample acquired by each capillary array 16, 150, 158, 168, 178.

The acquired sample was then eluted from the sample acquisition devices using three different techniques. As previously described, a sample was acquired by three devices including capillary array 16 formed of an SLA resin, three devices including capillary array 16 formed of polycarbonate, three devices including capillary array 16 formed of polypropylene, three devices including capillary array 16 formed of silicone rubber, three devices including capillary array 150, three devices including capillary array 158, three devices including capillary array 168, and three devices including capillary array 178. Thus, a different one of the three different sample release techniques were employed for a respective one of the devices including capillary arrays 16 formed of SLA resin, polycarbonate, polypropylene, and silicone rubber, as well as one a respective one of the devices including capillary arrays 168 158, 168, 178

In a first elution technique, sample acquisition devices including capillary array 16, 150, 158, 168, 178 were each vortexed in approximately 1 mL of a PBS elution buffer for approximately 30 seconds. The bacterial count eluted from the sample acquisition devices with the first technique are shown in FIG. 25 in the rows associated with the "Vortexing" elution method. In a second elution technique, the capillary array of the sample acquisition device was flushed by flowing approximately 1 mL of a PBS elution buffer through the lumen of the stem 12 of each sample acquisition device via a pipette, and capturing the flushed solution in a tube. The bacterial count eluted from the sample acquisition devices with the second technique are shown in FIG. 25 in the rows associated with the "Lumen Flush" elution method. In a third elution technique, each sample acquisition device was hand twirled in a PBS elution buffer for approximately 10 seconds. The bacterial count eluted from the sample acquisition devices with the third technique are shown in FIG. 25 in the rows associated with the "Hand Twirling" elution method.

The number of viable bacteria in each of the eluted samples was determined by plating serial dilutions of each sample on a ready-made culture medium system that includes Standard Methods nutrients, a cold-water-soluble gelling agent, and an indicator that facilitates colony enumeration, where the system is available under the name Petrifilm Aerobic Count Plates (from 3M Company of St. Paul, Minn.). The results of the experiment are shown in FIG. 25. The values reported in the table are the averages of three replicates for each type of sample acquisition device.

The percentage of bacteria released from the different capillary arrays 16, 150, 158, 168, and 178 was compared to a control bacterial count. In order to arrive at the control bacterial count, the bacterial concentration in approximately 0.1 mL of the bacterial suspension was determined. Based on the net weight of a respective one of the sample acquisition devices after the device was used to acquire a sample and the bacterial concentration in approximately 0.1 mL of the bacterial suspension, the quantity of bacteria acquired by the sample acquisition device was estimated. That is, the change in weight of the sample acquisition device after its capillary array was dipped in the bacterial solution reflects the volume of sample retained by the capillary array. The volume of sample retained may be compared to the concentration of bacteria in the sample in order to estimate the quantity of bacteria retained by the capillary array. This estimated quantity of bacteria was the control value.

The results shown in FIG. 25 suggest that when the sample was released from the sample acquisition devices via a vortexing technique, a sample acquisition device including capillary array 150 of FIG. 16A and device 10 including capillary array 16 formed of SLA resin released approximately similar quantities of viable bacteria (about 6580 and 6520 CFU/mL, respectively). In addition, capillary array 16 formed of an SLA resin and capillary array 150 released relatively large percentages of bacteria compared to their respective control values (approximately 105% and 118%, respectively) with the vortexing release technique. In some cases, the percentage of bacteria released from a capillary array was more than 100% of the control, i.e., more than 100% of the expected value based on the volume of sample acquired by the capillary array, due to variability attributable to counting bacteria.

When the sample was released from the sample acquisition devices via the lumen flush technique, a sample acquisition device including capillary array 16 formed of SLA resin and capillary array 16 formed of polycarbonate released the greatest quantity of viable bacteria (about 8080 and 7300 CFU/mL, respectively). Capillary array 16 formed of the SLA resin and capillary array 16 formed of polycarbonate also released relatively large percentages of bacterial compared to their respective control values (approximately 132% and 122%, respectively). In addition, capillary array 158 released approximately 148% of the captured bacteria, capillary array 168 released approximately 106% of the captured bacteria, and capillary array 178 released approximately 141% of the captured bacteria compared to their respective control values.

When the sample was released from the sample acquisition devices via the hand twirling technique, a sample acquisition device including capillary array 16 formed of polycarbonate released the greatest quantity of viable bacteria (about 9200 CFU/mL), while capillary array 16 formed of SLA resin, capillary array 16 formed of polypropylene, and capillary array 158 exhibited comparable release characteristics. Capillary array 16 released approximately 192% of captured bacteria compared to the control value. In comparison, capillary array 16 formed of SLA resin released approximately 133% of captured bacteria compared to the control value. Capillary array 16 formed of polypropylene released approximately 114% of captured bacteria compared to its control and capillary array 158 released approximately 131% of captured bacteria.

In general, data shown in FIG. 25 suggest that capillary arrays 16, 150, 158, 168, 178 exhibit efficient sample release characteristics. The data shown in FIG. 25 also suggests that capillary array 16 formed of SLA resin, capillary array 16 formed of polypropylene, capillary array 16 formed of polycarbonate, capillary array 158, and capillary array 178 exhibited better sample release characteristics when the sample was released from the respective capillary array via the hand twirling or lumen flushing techniques compared to the vortexing technique. In addition, the results shown in FIG. 25 suggest that substantially similar quantities of viable bacteria may be released from capillary array 168 with the vortexing, hand twirling, and lumen flushing elution techniques. However, in general, the volume of sample acquired by each of the capillary arrays may differ based on the type of material used to form the capillary arrays, as well as the design (e.g., dimensions, structure, etc.) of the capillary arrays.

FIG. 26 is a table that includes data analyzing the experimental data shown in FIG. 25. In particular, the table shown in FIG. 26 includes data comparing the average percentage of bacteria released for different parameters, i.e., elution technique, capillary array design or capillary array material, compared to a respective control, and the standard deviation between the three replicates of the experiment. As previously described, the control bacterial count was based on an estimated bacteria count, which was based on the volume of sample acquired by the capillary array. The table shown in FIG. 26 also illustrates the average weight of the sample retained by each capillary array design and capillary array material, as well as the standard deviation between the three replicates of the experiment.

The data shown in FIG. 26 suggests that the elution methods for releasing the sample from the capillary array did not significantly affect the percentage of bacteria released by each capillary array. This appears to indicate that the capillary arrays 16, 150, 158, 168, and 178 are generally capable of efficient release of the acquired sample, regardless of the elution method used. In addition, the data shown in FIG. 26 compares the percentage of bacteria released and average weight of sample acquired for the different capillary array designs. Capillary arrays 16, 150, 158, 168, and 178 acquired a wide range of sample weights, which is indicative of the acquired sample volumes. Capillary array 16 appeared capture the highest volume of sample relative to the other capillary array designs, thereby resulting in a relatively high quantity of eluted bacteria. However, the data suggests that, in general, the configuration of each capillary array 16, 150, 158, 168, and 178 resulted in efficient sample release.

The data shown in FIG. 26 also suggests that the material of the capillary array may impact the performance of capillary array. In particular, the sample acquisition and release performance for capillary arrays 16, which each had substantially similar structure but were formed of different materials, were compared. The capillary array 16 formed of the SLA resin acquired the greatest sample volume and released a larger quantity of bacteria. The SLA resin had the highest relative surface energy (approximately 50 dyn/cm) compared to the polypropylene, polycarbonate, and silicone rubber. The capillary array 16 formed of the silicone rubber, which had the lowest surface energy (approximately 20 dyn/cm), acquired the lowest sample volume, and released the lowest percentage of bacteria.

Various embodiments of the invention have been described. These and other embodiments are within the scope of the following claims. Reference to the orthogonal x-y-z axes throughout the present disclosure is used to aid the description of sample acquisition devices and is not intended to limit the scope of the present invention. In addition, in each of the embodiments including a capillary array and a stem, the capillary array and stem may be integral in some embodiments, while in other embodiments, the capillary array and stem may be separate elements that are coupled together.

The invention claimed is:

1. A sample acquisition device comprising:
    a stem defining a longitudinal axis extending in a first direction; and
    a capillary array coupled to the stem, wherein the capillary array comprises a major sample acquisition surface extending along a second direction different than the first direction;
    wherein the capillary array defines a plurality of concentric capillary channels.

2. The sample acquisition device of claim 1, wherein the second direction is substantially perpendicular to the first direction.

3. The sample acquisition device of claim 1, wherein at least a portion of the major sample acquisition surface is curvilinear.

4. The sample acquisition device of claim 1, wherein the capillary array comprises a plurality of structures defining a common sample acquisition region.

5. The sample acquisition device of claim 1, wherein the capillary array defines a plurality of sample acquisition regions.

6. The sample acquisition device of claim 1, wherein a ratio of the greatest dimension of the sample acquisition surface to a greatest dimension of the capillary array along the first direction is about 3:1 to about 100:1.

7. The sample acquisition device of claim 1, wherein the capillary array is configured to retain a maximum sample volume of about 0.025 milliliters to about 0.500 milliliters.

8. The sample acquisition device of claim 1, further comprising a tip coupled to the capillary array, wherein the tip defines a rounded sample acquisition surface.

9. The sample acquisition device of claim 1, further comprising a tip coupled to the capillary array, wherein the tip comprises a flexible portion that extends away from the sample acquisition surface.

10. The sample acquisition device of claim 1, further comprising a tactile feedback mechanism that indicates a relative amount of pressure applied by a user when engaging the capillary array with a sample source.

11. The sample acquisition device of claim 1, wherein the sample acquisition surface has an area of about 0.1 square centimeters ($cm^2$) to about 1.5 $cm^2$.

12. The sample acquisition device of claim 1, wherein a ratio of an area of the sample acquisition surface to the maximum sample volume is about 0.2 square centimeters per milliliter ($cm^2$/mL) to about 60 $cm^2$/mL.

13. The sample acquisition device of claim 1, wherein the capillary array is formed of a material comprising at least one of polysulfone, polycarbonate, polytetrafluoroethylene, polyvinylidene difluoride or nylon.

14. The sample acquisition device of claim 1, wherein the capillary array comprises a molded structure.

15. The sample acquisition device of claim 1, wherein the capillary array comprises a material comprising a surface energy of at least 20 dynes/centimeter.

16. The sample acquisition device of claim 1, wherein the surface energy of a material from which the capillary array is made is less than or equal to about 82 dynes/centimeter.

* * * * *

UNITED STATES PATENT AND TRADEMARK OFFICE
CERTIFICATE OF CORRECTION

PATENT NO. : 8,677,843 B2
APPLICATION NO. : 12/867146
DATED : March 25, 2014
INVENTOR(S) : Bernard A. Gonzalez et al.

It is certified that error appears in the above-identified patent and that said Letters Patent is hereby corrected as shown below:

In The Specification

Column 9,
Line 51, "$(P_r)$" should read --$(P_c)$--.

Column 16,
Line 28, "We" should read --$W_c$--.

Signed and Sealed this
Fifth Day of May, 2015

Michelle K. Lee
*Director of the United States Patent and Trademark Office*